United States Patent
Nakada et al.

(10) Patent No.: US 7,659,312 B2
(45) Date of Patent: Feb. 9, 2010

(54) INHIBITORS OF AQUAPORIN 4, METHODS AND USES THEREOF

(75) Inventors: Tsutomu Nakada, Niigata (JP); Vincent J. Huber, Niigata (JP)

(73) Assignee: Niigata University, Niigata (JP)

( * ) Notice: Subject to any disclaimer, the term of this patent is extended or adjusted under 35 U.S.C. 154(b) by 163 days.

(21) Appl. No.: 11/757,191

(22) Filed: Jun. 1, 2007

(65) Prior Publication Data

US 2007/0281978 A1    Dec. 6, 2007

(30) Foreign Application Priority Data

Jun. 1, 2006    (JP) ............................. 2006-154063

(51) Int. Cl.
*A61K 31/18*    (2006.01)
*C07C 303/00*    (2006.01)

(52) U.S. Cl. ........................................ 514/601; 564/80

(58) Field of Classification Search ................ 548/136, 548/165, 217, 229; 514/362, 367, 375, 376, 514/601; 564/80

See application file for complete search history.

(56) References Cited

U.S. PATENT DOCUMENTS

2008/0221169 A1*    9/2008    Flynn et al. .................. 514/351

FOREIGN PATENT DOCUMENTS

| WO | 0164219 | 9/2001 |
| WO | 2004/069181 A2 | 8/2004 |
| WO | 2005/094806 A1 | 10/2005 |

OTHER PUBLICATIONS

Huber et al., 1998, CAS: 129:202537.*
D. Binder, et al., Increased seizure threshhold in mice lacking aquaporin-4 water channel, NeuroReport, vol. 15, No. 2, Feb. 9, 2004, pp. 259-262.
N. Castle, Aquaporins as targets for drug discovery, Drug Discovery Today, vol. 10, No. 7, Apr. 2005, pp. 485-493.
B. Denker, et al., Identification, Purification, and Partial Characterization of a Novel Mr 28,000 Integral Membrane Protein from Erythrocytes and Renal Tubules, The Journal of Biological Chemistry, vol. 263, No. 30, Oct. 25, 1988, pp. 15634-15642.
T. Eid, et al., Loss of perivascular aquaporin 4 may underlie deficient water and K+ homeostasis in the human epileptogenic hippocampus, PNAS, vol. 102, No. 4, pp. 1193-1198, Jan. 25, 2005.
I. Johansson, et al., The role of aquaporins in cellular and whole plant water balance, Biochimica et Biophysica Acta, 1465, 2000, pp. 324-342.
J. Jung, Molecular characterization of an aquaporin cDNA from brain: Candidate osmoreceptor and regulator of water balance, Proc. Natl. Acad. Sci. USA, vol. 91, pp. 13052-13056, Dec. 1994.
M. Kuwahara, et al., Mercury-Sensitive Residues and Pore Site in AQP3 Water Channel, Biochemistry, vol. 36, No. 46, Nov. 18, 1997, pp. 13974-13978.

B. Ma, et al., Effects of acetazolamide and anordiol on osmotic water permeability in AQP1-cRNA injected *Xenopus* oocyte, Acta Pharmacologica Sinica, Jan. 25, 2004, pp. 90-97.
T. Muratake, et al., Linkage disequilibrium in aquaporin 4 gene and association study with schizophrenia, Psychiatry and Clinical Neurosciences (2005), 59, pp. 595-598.
G. Nicchia, et al., New possible roles for aquaporin-4 in astrocytes: cell cytoskeleton and functional relationship with connexin43, The FASEB Journal. FJ Express, vol. 19, Oct. 2005, pp. 1674-1676.
H. Tsukaguchi, et al., Functional and molecular characterization of the human neutral solute channel aquaporin-9, The American Physiological Sciety, 1999, pp. F685-F696.
Tajika, et al., 2005. "Differential regulation of AQP2 trafficking in endosomes by microtubules and actin filaments". Histochem Cell Biol 124: 1-12.
Detmers, et al., 2006. "Quaternary Ammonium Compounds as Water Channel Blockers". The Journal of Biological Chemistry vol. 280, No. 20, pp. 14207-14214.
Carmosino, et al., 2005. "Altered expression of aquaporin 4 and H+/K+ -ATPase in the stomachsof peptide YY (PYY) transgenic mice". Biol. Cell 97: 735-742.
Jimi, et al., 2004. "Reduced expression of aquaporin 4 in human muscles with amyotrophic lateral sclerosis and other neurogenic atrophies". Pathology—Research and Practice 200: 203-209.
Compton, et al., 2005. "The Syntrophin-Dystrobrevin Subcomplex in Human Neuromuscular Disorders". J. Neuropathol. Exp. Neurol. 64: 350-361.
Kenney, et al., 2004. "Altered Expression of Aquaporins in Bullous Keratopathy and Fuchs' Dystrophy Corneas". Journal of Histochemistry & Cytochemistry 52(10): 1341-1350.
Tenckhoff, et al., 2005. "Diversity of aquaporin mRNA expressed by rat and human retinas". NeuroReport 16(1): 53-56.
Verkman, A.S., 2003. "Role of aquaporin water channels in eye function". Experimental Eye Research 76: 137-143.
Briggman, et al., 2005. "Neuronal versus glial cell swelling in the ischaemic retina". Acta Ophtalmol. Scand. 83: 528-538.
Perez, et al., 2006. "Aquaporin expression in the cerebral cortex is increased at early stages of Alzheimer disease". Brain Research 1128: 164-174.
Li, et al., 2006. "Aquaporin-4 knockout regulated cocaine-induced behavior and neurochemical changes in mice". Neuroscience Letters 403: 294-298.
Lennon, et al., 2005. "IgG marker of optic-spinal multiple sclerosis binds to the aquaporin-4 water channel". Journal of Experimental Medicine 202(4): 473-477.
St. Hillaire, et al., 2005. "Aquaporin 4 is increased in association with human immunodeficiency virus dementia: Implications for disease pathogenesis". Journal of NeuroVirology 11: 535-543.
Alexander, et al., 2003. "Administration of the soluble complement inhibitor, Crry-Ig, reduces inflammation and aquaporin 4 expression in lupus cerebritis". Biochimica et Biophysica Acta 1639: 169-176.
Rodriguez, et al., 2006. "Increased expression of water channel aquaporin 1 and aquaporin 4 in Creutzfeldt-Jakob disease and in bovine spongiform encephalopathy-infected bovine-PrP transgenic mice". Acta Neuropathol. 112: 573-585.

(Continued)

*Primary Examiner*—Rei-tsang Shiao
(74) *Attorney, Agent, or Firm*—Darby & Darby PC

(57) ABSTRACT

This invention relates an inhibitory modulator of AQP4 protein regarding its transmembrane water transport properties, wherein the modulator selectively binds to the AQP4 protein, and inhibits AQP4 mediated water transport.

2 Claims, 7 Drawing Sheets

OTHER PUBLICATIONS

Papadopoulos, M. C., and Verkman, A. S., 2005. "Aquaporin-4 Gene Disruption in Mice Reduces Brain Swelling and Mortality in Pneumococcal Meningitis". The Journal of Biological Chemistry 280(14): 13906-13912.

Quick, A. M., Cipolla, M. J., 2005. "Pregnancy-induced up-regulation of aquaporin-4 protein in brain and its role in eclampsia". FASEB J. 19:170-175.

Warth, et al., 2005. "Redistribution of the water channel protein aquaporin-4 and the K+ channel protein Kir4.1 differs in low- and high-grade human brain tumors". Acta Neuropathol. 109: 418-426.

Saadoun, et al., 2003. "Water transport becomes uncoupled from K+ siphoning in brain contusion, bacterial meningitis, and brain tumours: immunohistochemical case review". J. Clin. Pathol. 56: 972-975.

Xiao, F., 2002. "Bench to Bedside: Brain Edema and Cerebral Resuscitation: The Present and Future". Acad. Emerg. Med. 9(9): 933-946.

Manley, et al., 2000. "Aquaporin-4 deletion in mice reduces brain edema after acute water intoxication and ischemic stroke". Nature Medicine 6(2): 159-163.

Aiko-Yoshino, et al., 2005. "Enhanced expression of aquaporin 4 in human brain with inflammatory diseases". Acta Neuropathol. 110: 281-288.

Amiry-Moghaddam, et al., 2004. "Alpha-syntrophin deletion removes the perivascular but not endothelial pool of aquaporin-4 at the blood-brain barrier and delays the development of brain edema in an experimental model of acute hyponatremia". FASEB J. 18: 542-544.

Papadopoulos, M. C., and Verkman, A. S., 2007. "Aquaporin-4 and brain edema". Pediatr. Nephrol.

Binder, D. K., and Steinhauser, C., 2006. "Functional Changes in Astroglial Cells in Epilepsy". GLIA 54: 358-368.

Tian, et al., 2005. "An astrocytic basis of epilepsy". Nature Medicine 11(9): 973-981.

Ito, et al., 2006. "Interleukin-1b induces the expression of aquaporin-4 through a nuclear factor-kB pathway in rat astrocytes". Journal of Neurochemistry 99: 107-118.

Simard, M., and Nedergaard, M., 2004. "The Neurobiology of Glia in the Context of Water and Ion Homeostasis". Neuroscience 129: 877-896.

Wang, et al., 2006. "Aquaporins as potential drug targets". Acta Pharmacologica Sinica 27(4): 395-401.

Kobayashi, et al., 2004. "Molecular Mechanisms and Drug Development in Aquaporin Water Channel Diseases: Aquaporins in the Brain". J. Pharmacol. Sci. 96: 264-270.

Zardoya, R., and Villalba, S., 2001. "A Phylogenetic Framework for the Aquaporin Family in Eukaryotes". J. Mol. Evol. 52: 391-404.

Hiroaki, et al., 2006. "Implications of the Aquaporin-4 Structure on Array Formation and Cell Adhesion". J. Mol. Biol. 355: 628-639.

Hasegawa, et al., 1994. "Molecular Cloning of a Mercurial-insensitive Water Channel Expressed in Selected Water-transporting Tissues". The Journal of Biological Chemistry 269(8): 5497-5500.

* cited by examiner

INHIBITORS OF AQUAPORIN 4, METHODS AND USES THEREOF

The present application claims priority under 35 U.S.C. §119 to Japanese Patent Application No. 2006-154063 filed on Jun. 1, 2006. The content of the application is incorporated herein by reference in its entirety.

FIELD OF THE INVENTION

The present invention relates to the identification of molecular inhibitors of Aquaporin 4 (AQP4), the means of identifying such compounds, and their applications thereof.

BACKGROUND OF THE INVENTION

Aquaporin 4 (AQP4) is a water specific member of the Aquaporin family of water and water/glycerol transporters (Hasegawa, et al. *J. Biol. Chem.* 1994, 269, 5497). The aquaporins are a structurally unique class of transmembrane transporter proteins, particularly compared to other transporters such as the sodium, calcium and chloride channels. Unlike the typical channel proteins, where the active channel is formed at the nexus of four or more protein monomers, the aquaporins are characterized by the formation of a protein homotetramer, where each protein monomer contains a channel that is virtually independent from that of the other protein monomers (Hiroaki, et al. *J. Mol. Bio.* 2006, 355, 628). The nexus of the AQP protein monomers is not believed to form an active channel or pore. Moreover, the significance of the aquaporin channel structure, versus that of other transmembrane channels, is not understood.

The AQP4 water transporter is widely distributed in the human body, with particularly high concentrations in the brain, eyes, ears, muscles, lungs and kidneys (Jung, et al. *Proc. Nat. Acad. Sci., USA* 1994, 91, 13052-13056). It is highly conserved among mammalian species, typically showing greater than 95% identity, and also has a similar biological distribution (Zardoya, et al. *J. Mol. Evol.* 2001, 52, 391). The main role of AQP4 is generally regarded to be the regulatory water balance of the tissues it is localized in.

Since the initial discovery of AQP4, chemical modulators thereof have been considered potential therapeutic agents for a variety of pathologies (Castle. *DDT* 2005, 10, 485; Kobayashi, et al. *J. Pharmacol. Sci.* 2004, 96, 264; Wang, et al. *Acta Pharmacol. Sin.* 2006, 27, 395). However, the relationship between AQP4 and disease may not be completely obvious, and in many cases may not reflect a pathological change in AQP4 expression or regulation. Indeed AQP4 plays a critical role in cellular migration and the cytoskeletal morphology of the tissues it is expressed in, and is also highly responsive to changes in the ionic strength of both the cytosol and extracellular fluid, and the function of the various transporters and enzymes that control that ionic strength (Simard, et al. *Neuroscience,* 2004, 129, 877). The use of pharmaceutical agents to modulate AQP4 function as a means of treating human disease has gained more relevance considering the recent understanding of how that function can be related to inflammation, in general (Ito, et al. *J. Neurochem.* 2006, 99, 107) and neuroresponse in particular (Tian, et al. Nat. Med. 2005, 11, 973; Binder, et al. *Glia* 2006, 54, 358).

The use of AQP4 modulators for the treatment of cerebral edema has been considered the most promising match for this target (Papadopoluos, et al. *Pediatr Nephrol.* 2007, in press). Currently the use of AQP4 inhibitors for the treatment of cytotoxic edema appears to be well supported (Amiry-Moghaddam, et al. *FASEB J.* 2004, 18, 542; Aoki-Yoshino, et al. *Acta Neuropathol.* 2005, 110, 281; Manley, et al. *Nat. Med.* 2000, 6, 159), while the treatment of vasogenic edema now appears to be contravened. The edema related conditions of ischemia (Xiao. *Acad. Emerg. Med.* 2002, 9, 933), brain tumors (Saadoun, et al. *J. Clin. Pathol.* 2003, 56, 972); Warth, et al. *Acta Neuropathol.* 2005, 109, 418), eclampsia (Quick, et al. *FASEB J.* 2005, 19, 170), meningitis (Papadopoulos, et al. *J. Biol. Chem.* 2005, 280, 13906), Creutzfeldt-Jakob disease (Rodriguez, et al. *Acta Neuropathol.* 2006, 112, 573), and lupus cerebritis (Alexander, et al. *Biochim. Biophys. Acta* 2003, 169) appear to be particularly well suited for pharmacological treatment by AQP4 modulators, based on the evidence of the biophysiological studies reported therein.

AQP4 modulating compounds have been suggested as medicants for the treatment of neurological disorders, particularly epilepsy (Binder, et al. *Neuroreport* 2004, 15, 259; Binder, et al. *Glia* 2006, 54, 358), human immunodeficiency virus related dementia (St Hillaire, et al. *J. Neurovirol.* 2005, 11, 535), neuromyelitis optica (Lennon, et al. *J. Exp. Med.* 2005, 202, 473) and drug addiction (Li, et al. *Neurosci. Lett.* 2006, 403, 294) based on the specifics of the disease pathology, results from biophysical studies or a combination thereof. More recent studies have shown the presence of significant AQP4 expressional upregulation in the early stages of Alzheimer disease (Pérez, et al. *Brain Res.* 2007, 1128, 164).

In addition to the cerebral and neurological disorders, a number of peripheral diseases have been found to share a relationship with AQP4. Ocular diseases relating to retinal ischemia (Bringmann, et al. *Acta Ophthalmol. Scand.* 2005, 83, 528), glaucoma (Verkman. *Exp. Eye Res.* 2003, 76, 137), proliferative retinopathy (Tenckhoff, et al. *Neuroreport* 2005, 16, 53) and bullous keratopathy (Kenney, et al. *J. Histochem. Cytochem.* 2004, 52, 1341) also appear to be related to AQP4 function, and hence can be considered as being in part treatable by direct AQP4 modulating agents. Muscular dystrophy is known to be directly related to problems associated with AQP4 localization and changes in its expression level (Compton, et al. *J. Neuropathol. Exp. Neurol* 2005, 64, 350, Jimi, et al. *Pathol. Res. Prac.* 2004, 200, 203); moreover, some classes of tumors overexpress AQP4 as part of their water recruitment process (Carmosino, et al. *Biol. Cell* 2005, 97, 735), both of which are considered potential therapeutic areas for AQP4 modulating agents.

To date, no pharmacologically relevant compounds have been demonstrated that are capable of directly inhibiting AQP4 in any assay system (either in vitro or in vivo). Recently, a patent application claiming a series of quaternary ammonium compounds as aquaporin inhibitors has been published (Deen, et al. PCT WO 2005/094806 A1, 2005). However, of the exemplary compounds, only tetraethyl ammonium chloride was shown to inhibit AQP4, and it appeared that compounds from that general class could not be considered as AQP4 inhibitors in any general sense. A similar result was also demonstrated in a subsequent paper (Detmers, et al. J. Biol. Chem. 2006, 281, 14207). Moreover, an earlier patent application has claimed the use of AQP inhibiting agents as therapeutic compounds for lowering interocular pressure, in the treatment of ophthalmologic diseases (Wax, PCT WO 2004/069181 A2, 2004). Again, no evidence was demonstrated regarding the particular types of compounds that would be able to inhibit AQP4, either specifically or as a pan-inhibitor of AQP isozymes. Nocodazole, in particular, was described as inhibiting the AQP4 mediated hypoosmotic expansion of HEK293 cells (van den Kieboom, et al. PCT WO 01/64219 A2, 2001); however, the HEK293 cell line expresses AQP4 amongst other AQP isozymes, and no data was shown to demonstrate which isozyme that molecule was interacting with. It is particularly relevant because nocodazole is a known inhibitor of AQP2 (Tajika, et al. *Histochem. Cell. Biol.* 2005, 124, 1), which is also expressed by the HEK293 cell line.

In addition to the compounds described above in the context of AQP4 inhibition, a number of modulators for other AQP isozymes were reported. Phloretin had had been described as being a pan inhibitor of several AQP subtypes (Tsukaguchi, et al. *J. Am. Physiol. Soc.* 1999, 277, F685), most notably AQP9, but there was no particular indication that this compound could be used to modulate the water transport of AQP4. AQP1 was shown to be inhibited in a dose dependent manner by the pan carbonic anhydrase inhibitor acetazolamide (Ma, et al., *Acta Pharmacol. Sin.* 2004, 25, 90). Many of the AQP transporter subtypes have also been shown to be inhibited by heavy metal salts (Kuwahara, et al., *Biochemistry* 1997, 36, 13973), presumably because of binding to an intra-pore cystine residue. However, AQP4 lacks such a residue in its pore region, and has also been shown to be insensitive to heavy metal inhibition (J Jung, et al. *Proc. Nat, Acad. Sci., USA* 1994, 91, 13052).

Hence at the time of this invention, pharmacologically relevant modulators of AQP4 were widely believed to be valuable as therapeutic agents; however, no potential agents had been identified.

SUMMARY OF THE INVENTION

According to a first aspect of the invention, there is proposed an inhibitory modulator of the AQP4 protein regarding its transmembrane water transport properties, wherein the modulator selectively binds to the AQP4 protein, and inhibits its ability to conduct water across the cellular membrane.

According to an additional aspect of the invention, there is proposed an inhibitory modulator of the AQP4 protein within the context of the first aspect, comprising an organic molecule of Formula I, $$R\text{—}Ar\text{—}SO_2NH_2 \qquad \text{Formula I}$$

wherein

Ar is selected from a group consisting of a 5- or 6-membered aromatic group and a 6,6-, 5,6- or 6,5-fused bicyclic aromatic group with or without one or more substituting nitrogen, oxygen and/or sulfur atoms;

R is selected from a group consisting of aliphatic, heteroaliphatic, aromatic, heteroaromatic, aliphatic-aromatic, aliphatic-heteroaromatic, heteroaliphatic-aromatic, heteroaliphatic-heteroaromatic, cycloaliphatic, and heterocycloaliphatic groups; and wherein the relative distribution of R and the sulfonamide group is such that they do not occupy the adjacent ring atom when Ar is a monocyclic sulfonamide.

According to an additional aspect of the invention, there is proposed an inhibitory modulator of the AQP4 protein within the context of the first aspect, comprising an organic molecule of Formula II,

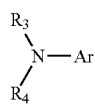

Formula II wherein

Ar is selected from a group consisting of a 5- or 6-membered aromatic group, a 6,6-, 5,6- or 6,5-fused bicyclic aromatic group with or without one or more substituting nitrogen, oxygen and/or sulfur atoms and a mono-substituted heterobicyclic aromatic group that contains at least one nitrogen atom;

$R_3$ is selected from a group consisting of proton, aliphatic, heteroaliphatic, aromatic, heteroaromatic, aliphatic-aromatic, aliphatic-heteroaromatic, heteroaliphatic-aromatic, heteroaliphatic-heteroaromatic, cycloaliphatic and heterocycloaliphatic groups and $R_5$—C(=O)—, $R_5$—NH—C(=O)—, $R_5$—O—C(=O)—, $R_5$—SO$_2$—, and $R_5$—; and $R_4$ and $R_5$ are independently selected from a proton, aliphatic, heteroaliphatic, aromatic, heteroaromatic, aliphatic-aromatic, aliphatic-heteroaromatic, heteroaliphatic-aromatic, heteroaliphatic-heteroaromatic, cycloaliphatic and heterocycloaliphatic groups.

According to a further aspect of the invention, there is proposed an inhibitory modulator of the AQP4 protein within the context of the first aspect, comprising an organic molecule of Formula III, $$R_6\text{—}X\text{—}Ar \qquad \text{Formula III}$$

wherein

Ar is selected from a group consisting of a 5- or 6-membered aromatic group, a 6,6-, 5,6- or 6,5-fused bicyclic aromatic group with or without one or more substituting nitrogen, oxygen and/or sulfur atoms and a mono-substituted heterobicyclic aromatic group that contains at least one nitrogen atom;

X is selected from a group consisting of —O—, —S—, —SO—, —SO$_2$—, —NR$_7$—C(=O)—, —NR$_7$—C(=O)—O— and —NR$_7$—SO$_2$—; and $R_6$ and $R_7$ are independently selected from a group consisting of proton, aliphatic, heteroaliphatic, aromatic, heteroaromatic, aliphatic-aromatic, aliphatic-heteroaromatic, heteroaliphatic-aromatic, heteroaliphatic-heteroaromatic, cycloaliphatic and heterocycloaliphatic groups.

According to a still further aspect of the invention, there is proposed an inhibitory modulator of the AQP4 protein within the context of the first aspect, comprising an organic molecule of Formula IV,

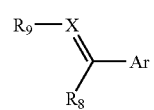

Formula IV wherein

Ar is selected from a group consisting of a 5- or 6-membered aromatic group, a 6,6-, 5,6- or 6,5-fused bicyclic aromatic group with or without one or more substituting nitrogen, oxygen and/or sulfur atoms and a mono-substituted heterobicyclic aromatic group that contains at least one nitrogen atom;

X is CH or N; and $R_8$ and $R_9$ are independently selected from a group consisting of proton, aliphatic, heteroaliphatic, aromatic, heteroaromatic, aliphatic-aromatic, aliphatic-heteroaromatic, heteroaliphatic-aromatic, heteroaliphatic-heteroaromatic, cycloaliphatic and heterocycloaliphatic groups.

According to a still further aspect of the invention, there is proposed an inhibitory modulator of the AQP4 protein within the context of the first aspect, comprising an organic molecule of Formula V,

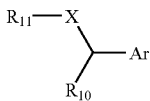

Formula V wherein

Ar is selected from a group consisting of a 5- or 6-membered aromatic group, a 6,6-, 5,6- or 6,5-fused bicyclic aromatic group with or without one or more substituting nitrogen, oxygen and/or sulfur atoms and a mono-substituted heterobicyclic aromatic group that contains at least one nitrogen atom;

X is —O—, —S—, —SO—, —SO$_2$—, —CH$_2$— or —NH—, or alternatively X is omitted such that $R_{10}$ and $R_{11}$ are geminal;

$R_{10}$ and $R_{11}$ are independently selected from a group consisting of proton, aliphatic, heteroaliphatic, aromatic, heteroaromatic, aliphatic-aromatic, aliphatic-heteroaromatic, heteroaliphatic-aromatic, heteroaliphatic-heteroaromatic, cycloaliphatic or heterocycloaliphatic.

According to another aspect of the invention, there is proposed an inhibitory modulator of the AQP4 protein within the context of the first aspect, comprising an organic molecule of Formula VI,

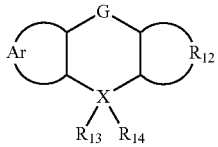

Formula VI wherein

Ar is an aromatic or heteroaromatic group with or without one or more aliphatic, heteratomic, and heteroaliphatic substitutions;

G is selected from a group consisting of proton, or an aliphatic or hetereoaliphatic spacer of one to three atoms in length;

X is carbon or nitrogen;

$R_{12}$ is aromatic or heteroaromatic with or without aliphatic or heteroaliphatic substitutions; or $R_{12}$ is selected from a group consisting of proton, aliphatic heteroaliphatic aliphatic-aromatic, heteroaliphatic-aromatic or aliphatic-heteroaromatic;

$R_{13}$ and $R_{14}$ are independently selected from a group consisting of proton, aliphatic, heteroaliphatic, aromatic, heteroaromatic, aliphatic-aromatic, aliphatic-heteroaromatic, heteroaliphatic-aromatic, heteroaliphatic-heteroaromatic, cycloaliphatic or heterocycloaliphatic, or any combination thereof, or $R_{13}$ and $R_{14}$ are connected by a spacer group that is selected from aliphatic, aromatic, heteroaliphatic, heteroaromatic or a combination thereof; and wherein $R_{14}$ is omitted to maintain the correct valence of the atom when X is a nitrogen atom.

According to a further aspect of the invention, there is proposed an inhibitory modulator of the AQP4 protein within the context of the first aspect, comprising an organic molecule of Formula VII,

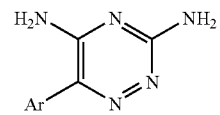

Formula VII wherein

Ar is selected from a group consisting of a 5- or 6-membered aromatic or heteroaromatic group, and a 6,6-, 5,6- or 6,5-membered fused bicyclic aromatic or heteroaromatic group with or without substitution with protons, aliphatic, heteroaliphatic and heteroatomic groups;

According to a still further aspect of the invention, there is proposed an inhibitory modulator of the AQP4 protein within the context of the first aspect, comprising an organic molecule of Formula VII,

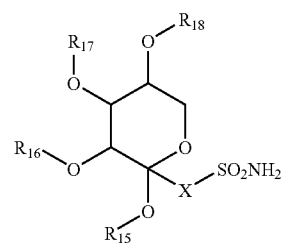

Formula VII wherein

X is an aliphatic or heteroaliphatic group;

$R_{15}$, $R_{16}$, $R_{17}$ and $R_{18}$ are selected from a group consisting of proton, and aliphatic or heteroaliphatic groups.

According to a still further aspect of the invention, there is proposed an inhibitory modulator of the AQP4 protein within the context of the first aspect, comprising an organic molecule of Formula VIII,

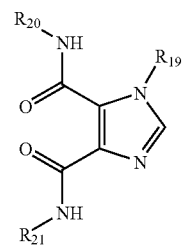

Formula VIII wherein $R_{19}$ $R_{20}$ and $R_{21}$ are independently selected from a group consisting of: proton, aliphatic, heteroaliphatic, aromatic, heteroaromatic, aliphatic-aromatic and aliphatic-heteroaromatic groups.

According to another aspect of the invention, there is proposed a therapeutic agent for the prevention, prophylaxis and treatment of disease pathology directly or indirectly related to AQP4 function comprising an inhibitory modulator of the AQP4 protein within the context of the foregoing aspects.

According to another aspect of the invention, there is proposed the use of an inhibitory modulator of the AQP4 protein within the context of the foregoing aspects as medicants for the treatment of human disease, wherein the inhibitory modulator of the AQP4 protein is utilized as a constitutive part of a polytherapy, and is combined as an individual component with one or more other pharmaceutically active agents, where each component interacts with a separate drug target, or alternatively as a single chemical agent that interacts preferentially with two or more drug targets, where one mode of action is the inhibition of AQP4 function.

According to a further aspect of the invention, there is proposed a therapeutic agent within the context of the previous aspects for the following uses: the treatment and prophylaxis of cerebral edema and the related pathologies, the prevention and prophylaxis of ischemia and ischemic injury, the treatment of encephalitis and diseases related thereto, the treatment and prophylaxis of neurological disease and the pathologies related thereto, the prophylaxis of epilepsy, seizure and involuntary convulsive disorders related thereto, the treatment and prophylaxis of bipolar disorder and psychological diseases related thereto, the treatment and prophylaxis of schizophrenia and psychological diseases related thereto, the treatment and prophylaxis of restless leg syndrome and diseases related thereto, the treatment and prophylaxis of diabetic neuropathy and morbidity related thereto, the treatment and prophylaxis of dystonia and disorders related thereto, the treatment of Huntington's disease, the treatment and prophylaxis of Parkinson's disease and the morbidity related thereto, the treatment and prophylaxis of migraine and pain disorders related thereto, the treatment and prophylaxis of dementia, the treatment of drug addition, the treatment and prophylaxis of ocular disease and the pathologies related thereto, the prevention and prophylaxis of retinal ischemia, the treatment and prophylaxis of glaucoma, the treatment of proliferative retinopathy and pathology related thereto, the treatment of bullous keratopathy and complications thereof, the treatment of tumors and cancerous growths and morbidity related thereto as would be understood by a practitioner of normal skill in the art, or the treatment and prophylaxis of Meniere's disease and pathology related thereto.

DETAILED DESCRIPTION OF THE INVENTION

Figure 1:
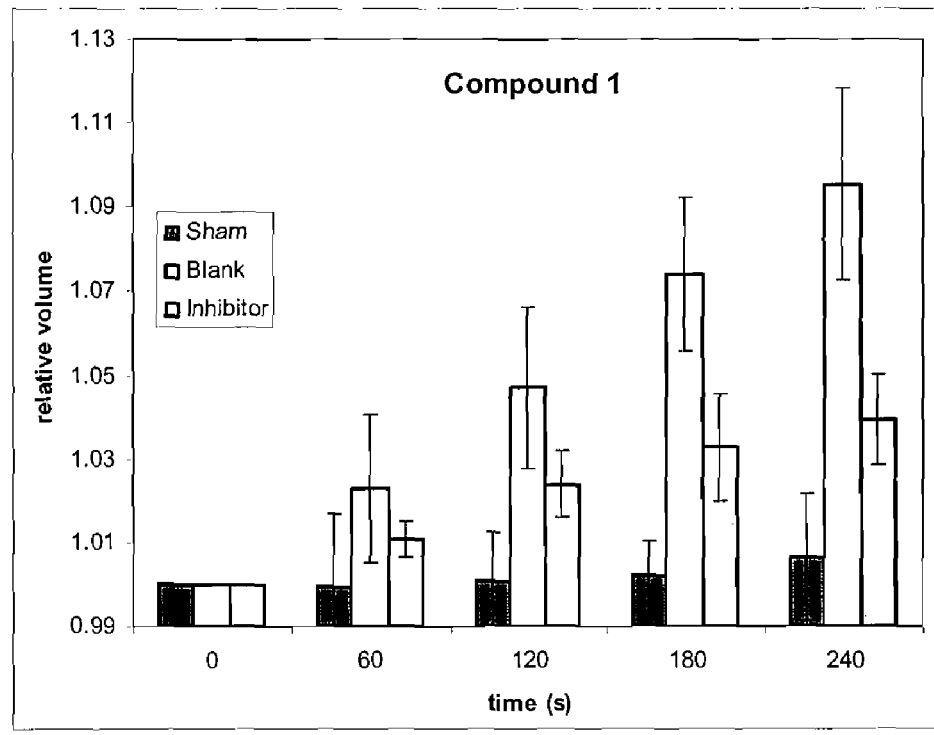
FIGS. 1-6 are schematic drawings showing the degree of inhibition of AQP4 mediated water swelling in xenopus oocytes transfected to express this transmembrane channel protein under hypoosmotic conditions in the presence of a 20 µM solution containing the inhibitor compound. The figures are labeled with Sham, Blank, Inhibitor to indicate the time course of relative volumetric changes experienced by oocytes injected with water, AQP4 mRNA with no inhibitor added and AQP4 mRNA with inhibitor added, respectively. The error bars shown represent the standard deviations at that time point for a minimum of n=5 replications. The compounds described in FIGS. 1-5 show statistically significant inhibition of AQP4 mediated water transport compared to the sham and blank prepared oocytes. Compound 6 did not show a significantly inhibited water transport compared to the sham and blank prepared oocytes.
Figure 2:
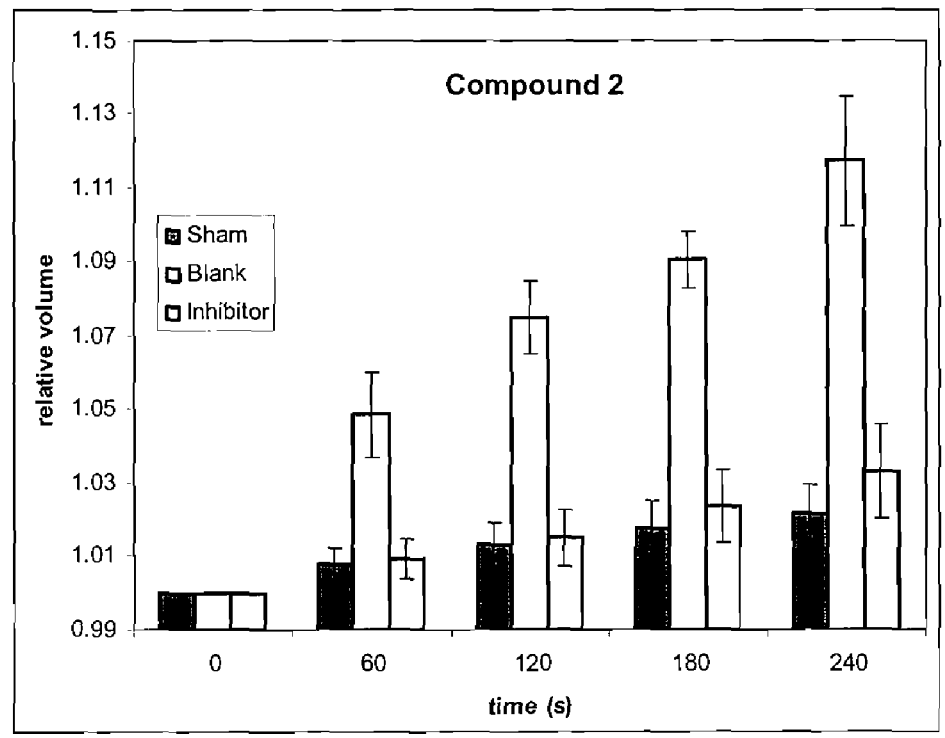
Figure 3:
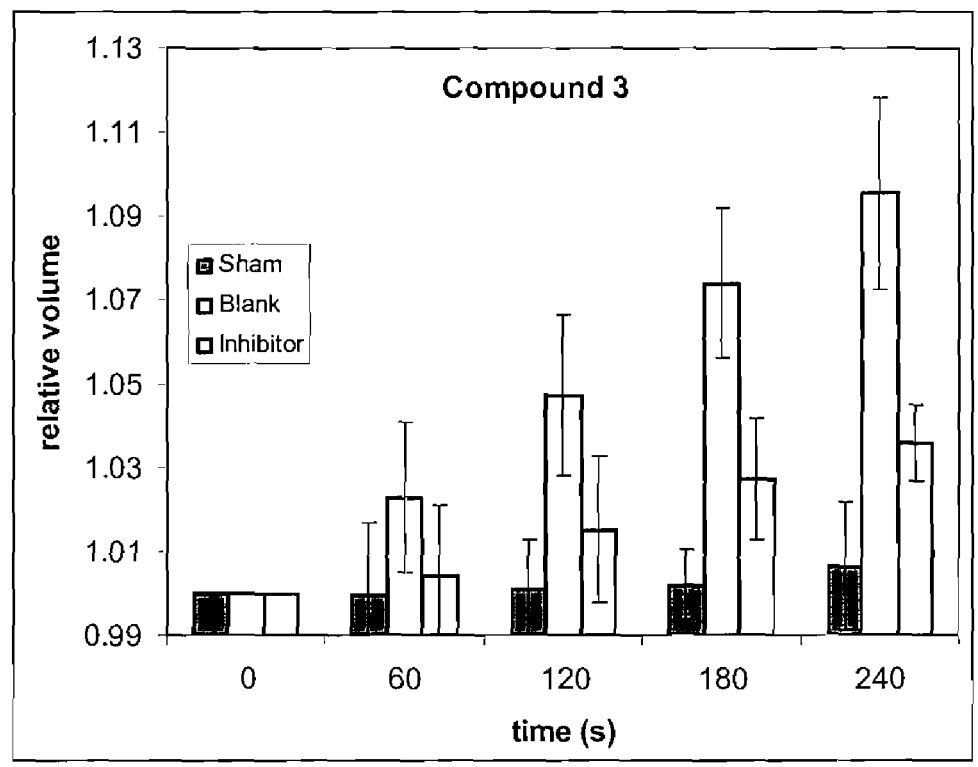
Figure 4:
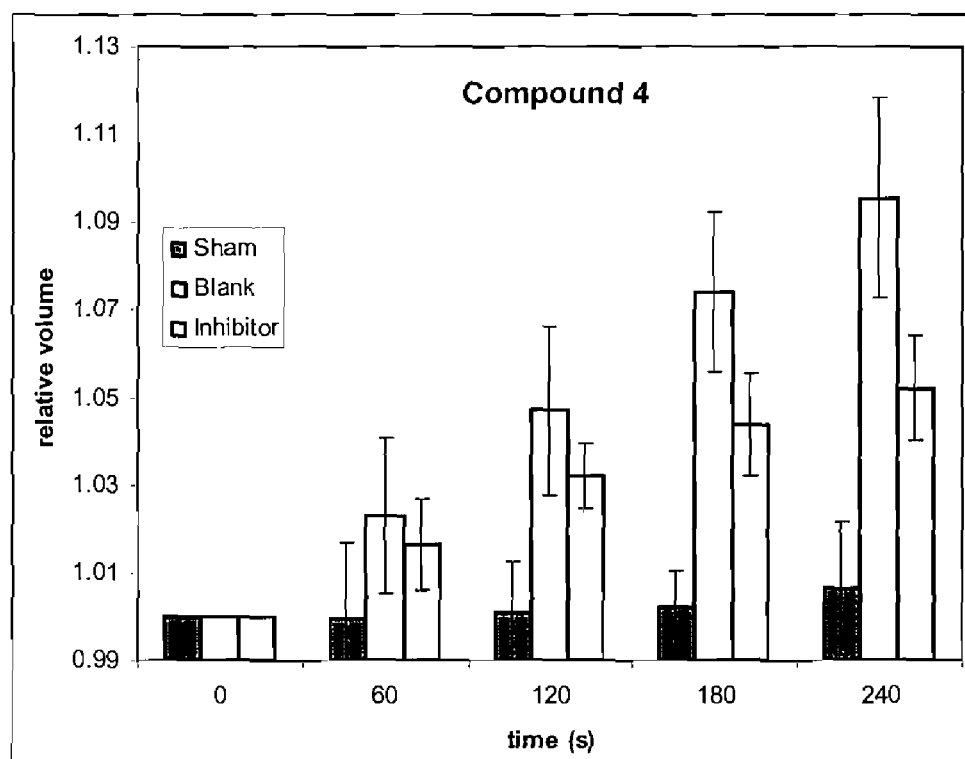
Figure 5:
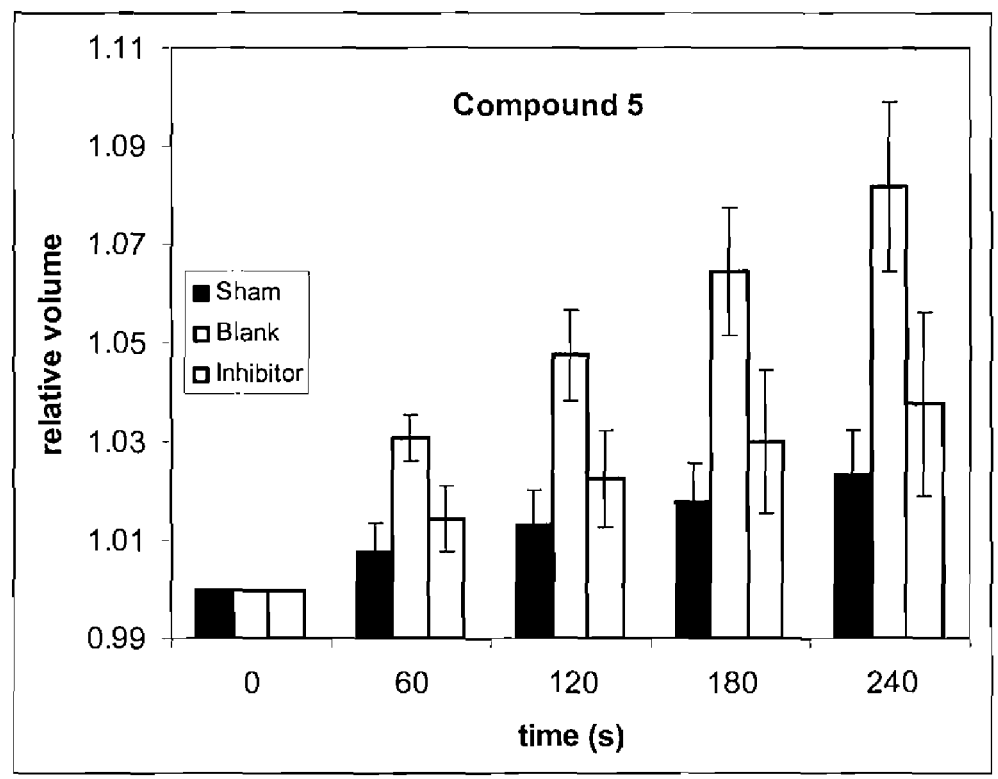
Figure 6:
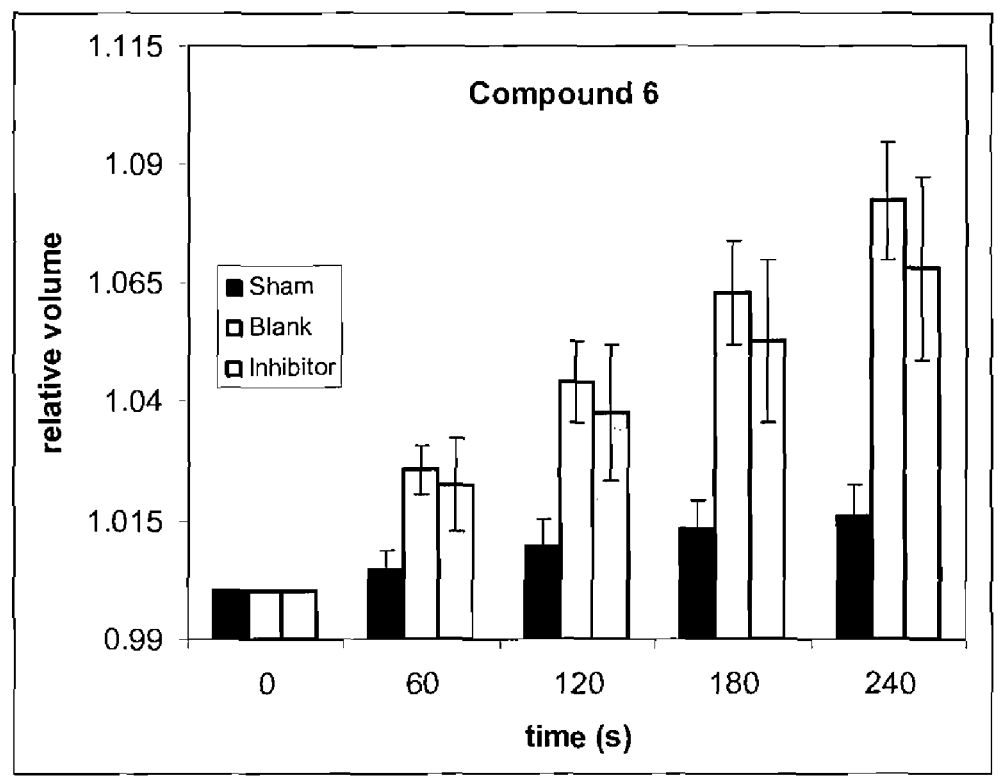
Figure 7:
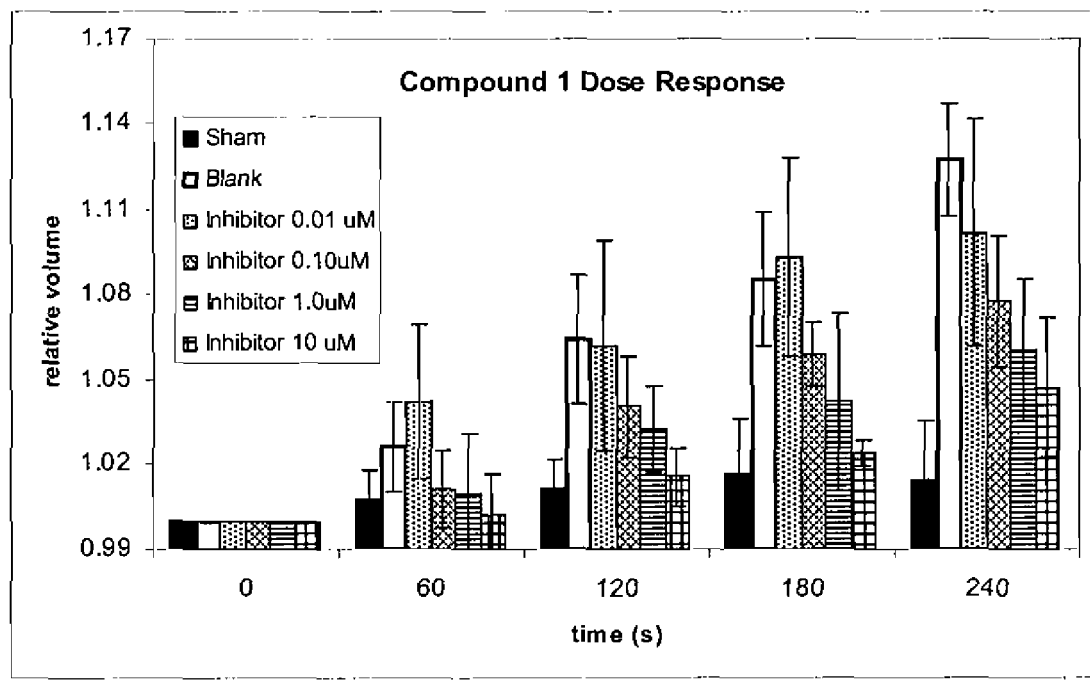
FIG. 7 is a representative drawing of the dose response dependent inhibition of AQP4 mediated water swelling in *Xenopus* oocytes transfected to express this transmembrane channel protein under hypoosmotic conditions. The concentrations of the inhibitor are indicated in the figure. Also included in the figure are Sham and Blank, which represent the oocytes injected with water, and AQP4 mRNA in the absence of an inhibitory compound, respectively. Error bars represent the standard deviation at that time point for n=5 replications. In this representation, significant inhibition of the AQP4 mediated water transport were observed after contact of the AQP4 mRNA injected oocytes with 0.01, 0.1, 1.0 and 10 µM solutions of inhibitor 1.

The following examples are intended to illustrate the general level of skill necessary to utilize the embodiments of the invention in the identification of Aquaporin 4 inhibitors. These examples are not intended to limit the scope of the invention or the claims thereof beyond that which has been described therein.

Example 1

This Example 1 concerns organic chemical agents of synthetic or natural origin, or a combination thereof, and their pharmaceutically relevant salts and derivatives as inhibitory modulators of the AQP4 protein and its transmembrane water transport properties. Such molecular agents can have a variety of uses in medicine, pharmacology and drug discovery.

In this example, there is further proposed the class of organic molecules and their pharmaceutically acceptable salts wherein they may be described by the following schematic diagram:

R—Ar—SO$_2$NH$_2$

Within the context of this example, Ar may be described as a 5- or 6-membered aromatic group that may contain nitrogen, oxygen or sulfur, in addition to carbon and hydrogen atoms. Ar can also be described as a 6,6-, 5,6- or 6,5-fused bicyclic aromatic group that may contain nitrogen, oxygen and sulfur, in addition to carbon and hydrogen atoms. Preferred in this example is the relative distribution of the R and sulfonamide groups such that they do not occupy the adjacent ring atom when Ar is a monocyclic sulfonamide, wherein for 6-atom aromatic rings those groups may be described as being meta or para to each other, and for 5-atom aromatic rings those groups may be described as having a 1-3 relationship. As examples of the types of groups preferred within the context of the example, Ar—SO$_2$NH$_2$ group can then be described as being from but not limited to members of the following list: 4-substituted benzene-1-sulfonamide; 3-substituted benzene-1-sulfonamide; 4-substituted pyridine-2-sulfonamide; 5-substituted pyridine-2-sulfonamide; 6-substituted pyridine-2-sulfonamide; 2-substituted pyrazine-5-sulfonamide; 5-substituted pyrimidine-2-sulfonamide; 5-substituted thiophene-2-sulfonamide; 4-substituted thiophene-2-sulfonamide; 5-substituted oxazole-2-sulfonamide; 4-substituted oxazole-2-sulfonamide; 5-substituted thiaziazole-2-sulfonamide; 4-substituted thiaziazole-2-sulfonamide; 2-substituted oxadiazole-5-sulfonamide; 2-substituted thiazole-5-sulfonamide; 2-substituted imidizole-4-sulfonamide; 3-substituted isoxazole-5-sulfonamide; 1-substituted diazole-3-sulfonamide; 5-substituted benzothiazole-2-sulfonamide; 6-substituted benzothiazole-2-sulfonamide; 5-substituted benzoxazole-2-sulfonamide; 6-substituted benzoxazole-2-sulfonamide. Ar groups as described herein can be further substituted with alkyl, heteroalkyl or heteroatoms in available open positions, as would be obvious to practitioners of normal skill in the art.

Within the context of this example, R may be described as being aliphatic, heteroaliphatic, aromatic, heteroaromatic, aliphatic-aromatic, aliphatic-heteroaromatic, heteroaliphatic-aromatic, heteroaliphatic-heteroaromatic, cycloaliphatic or heterocycloaliphatic, or alternatively composed of R'—C(=O)—NR"—, R'—NH—C(=O)—NR"—, R'—O—C(=O)—NR"— or R'—NR"—, where R' or R" can individually be described as being a proton, aliphatic, heteroaliphatic, aromatic, heteroaromatic, aliphatic-aromatic, aliphatic-heteroaromatic, heteroaliphatic-aromatic, heteroaliphatic-heteroaromatic, cycloaliphatic or heterocycloaliphatic. In the case where either of the R' or R" groups forms a stereogenic center, that stereocenter may be either chiral or racemic. Within the context of this example, R may be further described as being composed of R'—C(=O)—O—, R'—NH—C(=O)—O—, R'—SO$_2$—NH—, R'—O—, R'—S—, or R'—SO$_2$—, where R' can described as being a proton, aliphatic, heteroaliphatic, aromatic, heteroaromatic, aliphatic-aromatic, aliphatic-heteroaromatic, heteroaliphatic-aromatic, heteroaliphatic-heteroaromatic, cycloaliphatic or heterocycloaliphatic. Moreover, in the case where the R' group forms a stereogenic center, that stereocenter may be either chiral or racemic.

The following structures are intended as representative examples of chemical agents described herein but should not be construed as limiting this example beyond that described above.

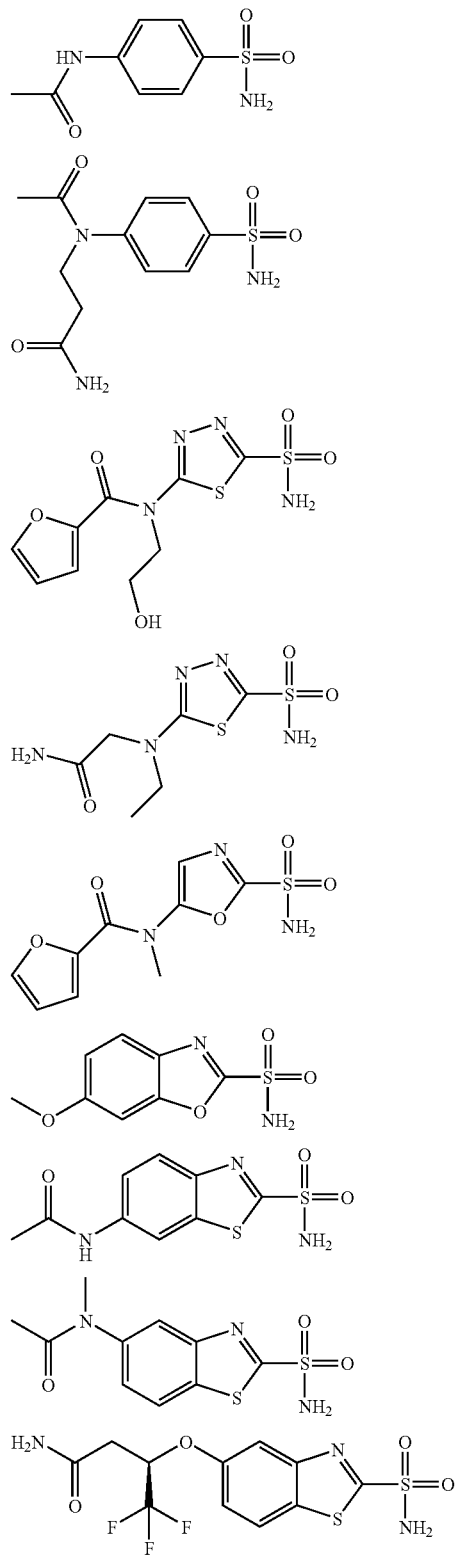

Example 3

As a further embodiment of Example 1, we propose the class of organic molecules and their pharmaceutically acceptable salts wherein they may be described by the following schematic diagram:

Within the context of this example, Ar may be described as a 5- or 6-membered aromatic group that may contain nitrogen, oxygen or sulfur, in addition to carbon and hydrogen atoms. Ar can also be described as being a 6,6-, 5,6- or 6,5-fused bicyclic aromatic group that may contain nitrogen, oxygen and sulfur, in addition to carbon and hydrogen atoms. Preferred in this example are Ar groups that contain one or more ring nitrogen atoms that can not be described as being —NH— or —$NH_2^+$—. As examples of the types of groups preferred within the context of this example, the Ar group can then be described as being selected from but not limited to the following list: 3-substituted pyridine; 2-substituted pyrazine; 5-substituted pyrimidine; 2-substituted oxazole; 5-substituted oxazole; 2-substituted thiodiazole; 2-substituted oxadiazole; 2-substituted thiazole; 5-substituted thiazole; 5-substituted imidizole; 3-substituted 1,2-diazole; 4-substituted 1,2-diazole; 5-substituted 1,2-diazole; 3-substituted isothiazole; 4-substituted isothiazole; 5-substituted isothiazole; 3-substituted isoxazole; 4-substituted isoxazole; 5-substituted isoxazole. Within the context of this example, Ar can also be described as being a mono-substituted heterobicyclic aromatic group that contains at least one nitrogen atom. Specifically, Ar can also be comprised by a member from the following list: 5-substituted benzothiazole; 6-substituted benzothiazole; 5-substituted benzoxazole; 6-substituted benzoxazole; 5-substituted benzimidazole; 6-substituted cinnoline; 7-substituted cinnoline; 6-substituted quinoxaline; 6-substituted quinazoline; 7-substituted quinazoline; 6-substituted napthyridine; 7-substituted napthyridine; 2-substituted napthyridine. Also within the context of this example, Ar can connected to R' by means of an aliphatic, heteroaliphatic, aliphaticaromatic or heteroaliphaticaromatic group, such that the resulting ring structure is composed of 6-, 7- or 8-atoms. Ar groups described herein can be further substituted by alkyl, heteroalkyl and heteroatoms as would be obvious to practitioners of normal skill in the art.

Within the context of this example, R may be described as being proton, aliphatic, heteroaliphatic, aromatic, heteroaromatic, aliphatic-aromatic, aliphatic-heteroaromatic, heteroaliphatic-aromatic, heteroaliphatic-heteroaromatic, cycloaliphatic or heterocycloaliphatic. Alternatively, R can be composed of R"—C(═O)—, R"—NH—C(═O)—, R"—O—C(═O)—, R"—$SO_2$—, or R"—. Furthermore, R' or R" may be described as being a proton, aliphatic, heteroaliphatic, aromatic, heteroaromatic, aliphatic-aromatic, aliphatic-heteroaromatic, heteroaliphatic-aromatic, heteroaliphatic-heteroaromatic, cycloaliphatic or heterocycloaliphatic. In the case where either of the R' or R" groups forms a stereogenic center, that stereocenter may be either chiral or racemic. In the context of this Example R' and R" may either be identical or non-equivalent, and may be connected by a bridging group composed totally or in part by an aliphatic or aromatic moiety to form an additional cyclic structure.

The following structures are intended as representative examples of chemical agents described herein but should not be construed as limiting this example beyond that described above.

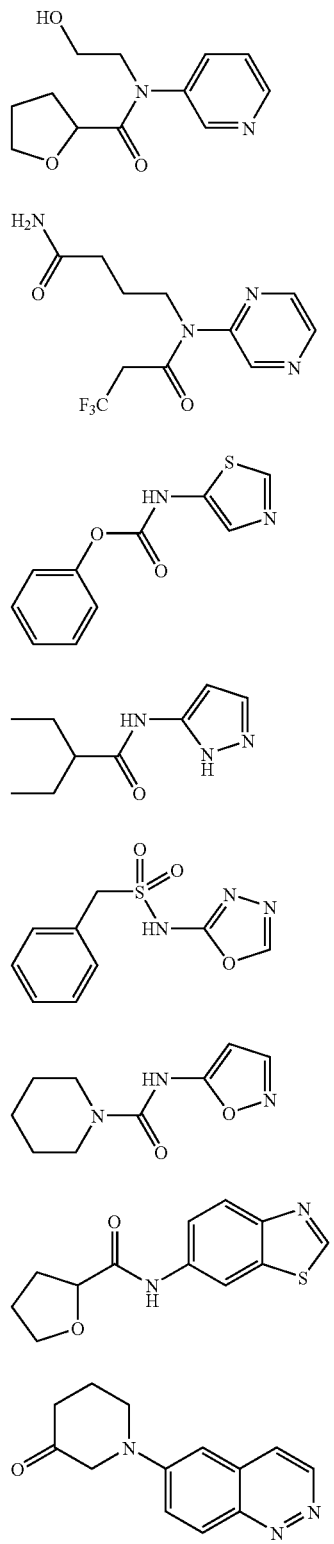

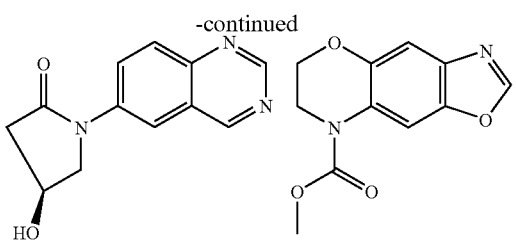

Example 4

As a further embodiment of Example 1, we propose the class of organic molecules and their pharmaceutically acceptable salts wherein they may be described by the following schematic diagram:

Within the context of this example, Ar may be described as being a 5- or 6-membered aromatic group that may contain nitrogen, oxygen or sulfur, in addition to carbon and hydrogen atoms. Ar may also be described as being a 6,6-, 5,6- or 6,5-fused bicyclic aromatic group that may contain nitrogen, oxygen and sulfur, in addition to carbon and hydrogen atoms. Preferred in this example are Ar groups that contain one or more ring nitrogen atoms that can not be described as being —NH— or —$NH_2^+$—. As examples of the types of groups preferred within the context of this embodiment of the example, the Ar group can then be described as being selected from but not limited to the following list: 3-substituted pyridine; 2-substituted pyrazine; 5-substituted pyrimidine; 2-substituted oxazole; 5-substituted oxazole; 2-substituted thiodiazole; 2-substituted oxadiazole; 2-substituted thiazole; 5-substituted thiazole; 5-substituted imidizole; 3-substituted 1,2-diazole; 4-substituted 1,2-diazole; 5-substituted 1,2-diazole; 3-substituted isothiazole; 4-substituted isothiazole; 5-substituted isothiazole; 3-substituted isoxazole; 4-substituted isoxazole; 5-substituted isoxazole. Within this context of the example, Ar may also be described as being a mono-substituted heterobicyclic aromatic group that contains at least one nitrogen atom. Specifically, Ar may also be comprised by a member from the following list: 5-substituted benzothiazole; 6-substituted benzothiazole; 5-substituted benzoxazole; 6-substituted benzoxazole; 5-substituted benzimidazole; 6-substituted cinnoline; 7-substituted cinnoline; 6-substituted quinoxaline; 6-substituted quinazoline; 7-substituted quinazoline; 6-substituted napthyridine; 7-substituted napthyridine; 2-substituted napthyridine. Ar groups described herein may be further substituted by alkyl, heteroalkyl and heteroatoms as would be obvious to practitioners of normal skill in the art.

Within the context of this example, R and R' may be described as being proton, aliphatic, heteroaliphatic, aromatic, heteroaromatic, aliphatic-aromatic, aliphatic-heteroaromatic, heteroaliphatic-aromatic, heteroaliphatic-heteroaromatic, cycloaliphatic or heterocycloaliphatic. Also within the context of this example, X may be described as being —O—, —S—, —SO—, —$SO_2$—, —NR'—C(=O)—, —NR'—C(=O)—O— or —NR'—$SO_2$—. In the case where either the R or R' group forms a stereogenic center, that stereocenter may be either chiral or racemic. The R and R' groups may additionally be connected by a bridging group totally or in part composed of aliphatic or aromatic moieties.

The following structures are intended as representative examples of chemical agents described herein but should not be construed as limiting this example beyond that described above.

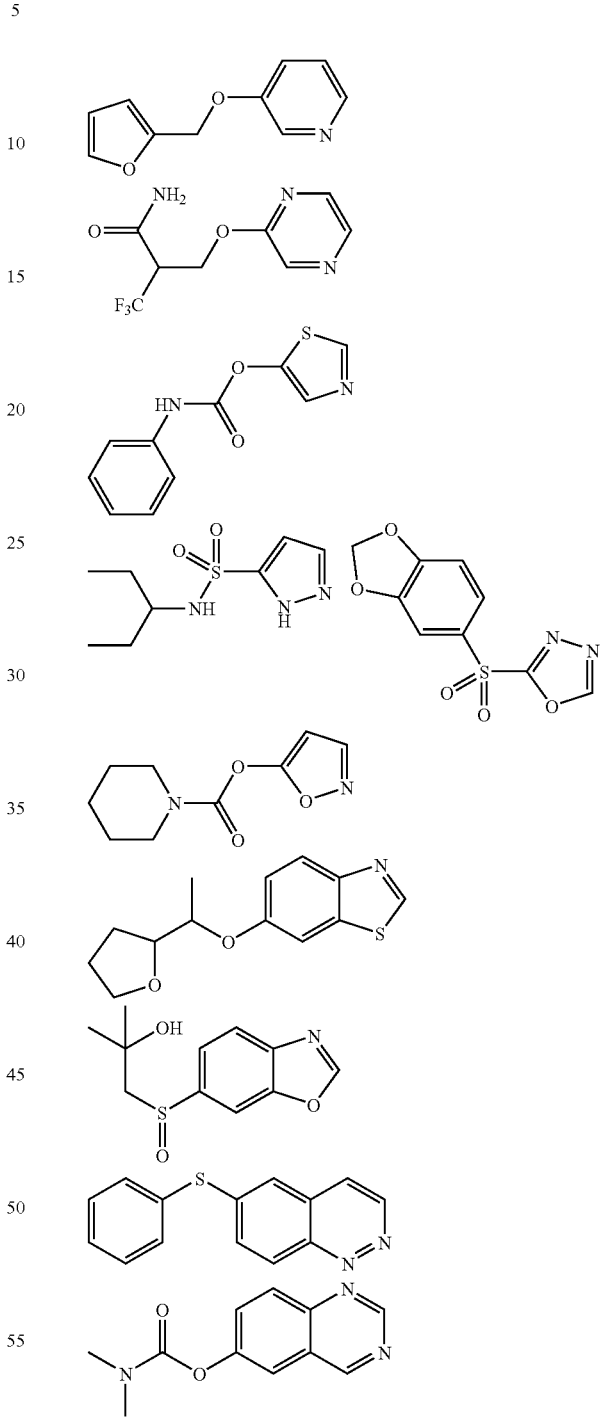

Example 5

As a further embodiment of Example 1, we propose the class of organic molecules and their pharmaceutically acceptable salts wherein they may be described by the following schematic diagram:

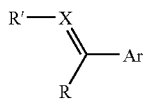

Within the context of this example, Ar may be described as a 5- or 6-membered aromatic group that may contain nitrogen, oxygen or sulfur, in addition to carbon and hydrogen atoms. Ar may also be described as being a 6,6-, 5,6- or 6,5-fused bicyclic aromatic group that may contain nitrogen, oxygen and sulfur, in addition to carbon and hydrogen atoms. Preferred in this example are Ar groups that contain one or more ring nitrogen atoms that can not be described as being —NH— or —NH$_2^+$—. As examples of the types of Ar groups preferred within the context of this example, the Ar group may then be described as being selected from but not limited to the following list: 3-substituted pyridine; 2-substituted pyrazine; 5-substituted pyrimidine; 5-substituted oxazole; 2-substituted thiadiazole; 2-substituted oxadiazole; 5-substituted thiazole; 5-substituted imidizole; 1-substituted imidazole; 5-substituted diazole; 4-substituted isothiazole; 5-substituted isothiazole; 4-substituted isoxazole; 5-substituted isoxazole. This embodiment of the Example also includes other aromatic groups, where Ar is a mono-substituted heterobicyclic aromatic group that contains at least one nitrogen atom. Ar may then also be comprised by a member from the following list: 5-substituted benzothiazole; 6-substituted benzothiazole; 5-substituted benzoxazole; 6-substituted benzoxazole; 5-substituted benzimidazole; 6-substituted cinnoline; 7-substituted cinnoline; 6-substituted quinoxaline; 6-substituted quinazoline; 7-substituted quinazoline; 6-substituted napthyridine; 7-substituted napthyridine; 2-substituted napthyridine. Ar groups described herein may be further substituted by alkyl, heteroalkyl and heteroatoms as would be obvious to practitioners of normal skill in the art.

Within the context of this example, X may be described as being CH or alternatively as N. Within the context of the example, R and R' may be described as being proton, aliphatic, heteroaliphatic, aromatic, heteroaromatic, aliphatic-aromatic, aliphatic-heteroaromatic, heteroaliphatic-aromatic, heteroaliphatic-heteroaromatic, cycloaliphatic or heterocycloaliphatic. In the case where either of the R or R' groups forms a stereogenic center, that stereocenter may be either chiral or racemic. R and R' may either be identical or non-equivalent, and may be connected Ar by a bridging group composed totally or in part by an aliphatic or aromatic moiety to form an additional cyclic structure. In the case where X is defined by CH, the resulting olefin may have either an E or Z distribution.

The following structures are intended as representative examples of chemical agents described herein but should not be construed as limiting this example beyond that described above.

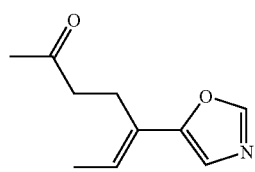

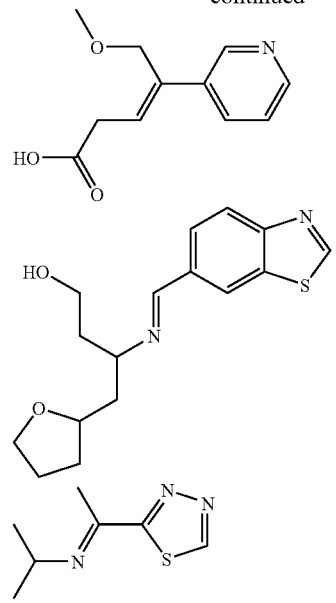

Example 6

As a further embodiment of Example 1, we propose the class of organic molecules and their pharmaceutically acceptable salts wherein they may be described by the following schematic diagram:

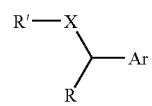

Within the context of this example, Ar may be described as a 5- or 6-membered aromatic group that may contain nitrogen, oxygen or sulfur, in addition to carbon and hydrogen atoms. Additionally, Ar may be described as being a 6,6-, 5,6- or 6,5-fused bicyclic aromatic group that may contain nitrogen, oxygen and sulfur, in addition to carbon and hydrogen atoms. Preferred in this example are Ar groups that contain one or more ring nitrogen atoms that can not be described as being —NH— or —NH$_2^+$—. As examples of the types of Ar groups preferred within the context of this example, the Ar group may be described as being selected from but not limited to the following list: 3-substituted pyridine; 2-substituted pyrazine; 5-substituted pyrimidine; 5-substituted oxazole; 2-substituted thiadiazole; 2-substituted oxadiazole; 5-substituted thiazole; 5-substituted imidizole; 1-substituted imidazole; 5-substituted diazole; 4-substituted isothiazole; 1-substituted triazole; 5-substituted isothiazole; 4-substituted isoxazole; 5-substituted isoxazole. This embodiment of the example also includes other aromatic groups, where Ar is a mono-substituted heterobicyclic aromatic group that contains at least one nitrogen atom. Ar may then also be describes as being but not limited to a member from the following list: 5-substituted benzothiazole; 6-substituted benzothiazole; 5-substituted benzoxazole; 6-substituted benzoxazole; 5-substituted benzimidazole; 6-substituted cinnoline; 7-substituted cinnoline; 6-substituted quinoxaline; 6-substituted quinazoline; 7-substituted quinazoline; 6-substituted napthyridine; 7-substituted napthyridine; 2-substituted napthyridine. Ar groups described herein may be further substituted by alkyl, heteroalkyl and heteroatoms as would be obvious to practitioners of normal skill in the art.

Within the context of this example, X may be described as being —O—, —S—, —SO—, —SO$_2$—, —CH$_2$— or —NH—, or alternatively X may be omitted such that R and R' are geminal. Within the context of the example, R and R' may be described as being proton, aliphatic, heteroaliphatic, aromatic, heteroaromatic, aliphatic-aromatic, aliphatic-heteroaromatic, heteroaliphatic-aromatic, heteroaliphatic-heteroaromatic, cycloaliphatic or heterocycloaliphatic. In the case where either of the R or R' groups forms a stereogenic center, that stereocenter may be either chiral or racemic. R and R' may either be identical or non-equivalent, and may be connected to each other or to Ar by a bridging group composed totally or in part by an aliphatic or aromatic moiety to form an additional cyclic structure.

The following structures are intended as representative examples of chemical agents described herein but should not be construed as limiting this example beyond that described above.

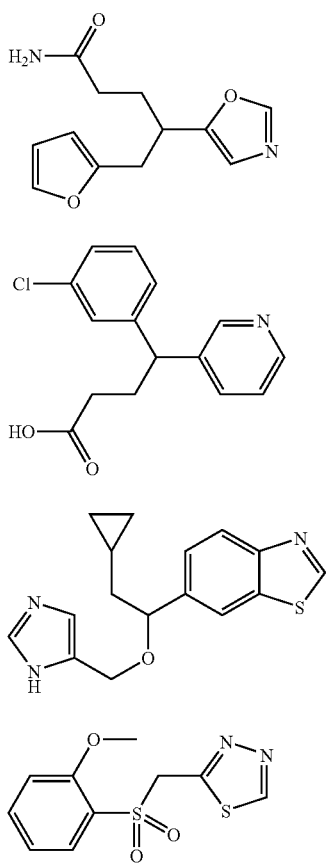

Example 7

As a further embodiment of Example 1, we propose the class of organic molecules and their pharmaceutically acceptable salts wherein they may be described by the following schematic diagram:

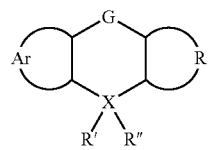

Within the context of this example, Ar may be described as being an aromatic or heteroaromatic group, and may contain further aliphatic, heteratomic, and heteroaliphatic substitutions. R may be described as being aromatic or heteroaromatic, which may contain further aliphatic or heteroaliphatic substitutions, alternatively R may be described as being proton, aliphatic heteroaliphatic aliphatic-aromatic, heteroaliphatic-aromatic or aliphatic-heteroaromatic. G may be described as being proton, as would describe a situation where no bridge existed between Ar and R, or alternatively as being an aliphatic or hetereoaliphatic spacer of one to three atoms in length. Within the context of this example, X may be described as being carbon or nitrogen. Within this context, R' and R" may be described as being proton, aliphatic, heteroaliphatic, aromatic, heteroaromatic, aliphatic-aromatic, aliphatic-heteroaromatic, heteroaliphatic-aromatic, heteroaliphatic-heteroaromatic, cycloaliphatic or heterocycloaliphatic, or any combination thereof. R' and R" may also be connected by a spacer group that may be described as being aliphatic, aromatic, heteroaliphatic, heteroaromatic or a combination thereof. When X is described as being a nitrogen atom R" may be omitted to maintain the correct valence of the atom. In the case where either of the R, R' or R" groups forms a stereogenic center, that stereocenter may be either chiral or racemic.

The following structures are intended as representative examples of chemical agents described herein but should not be construed as limiting this example beyond that described above.

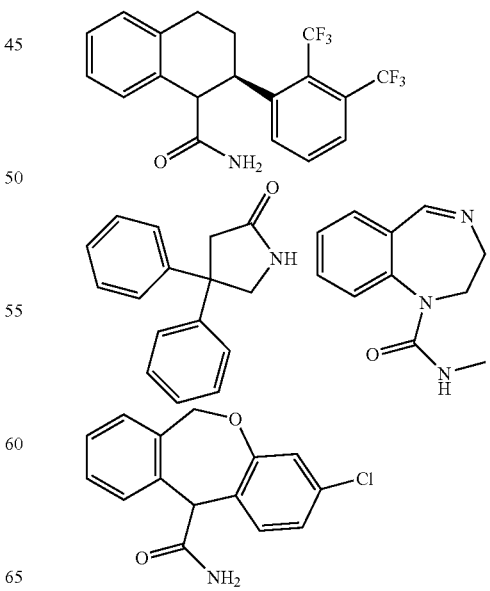

Example 8

As a further embodiment of Example 1, we propose the class of organic molecules and their pharmaceutically acceptable salts wherein they may be described by the following schematic diagram:

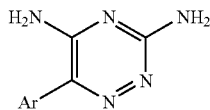

Within the embodiment of this example, Ar may be described as a 5- or 6-membered aromatic or heteroaromatic group, or alternatively as being a 6,6-, 5,6- or 6,5-membered fused bicyclic aromatic or heteroaromatic. Ar may be further substituted with protons, aliphatic, heteroaliphatic and heteroatomic groups. Chiral centers formed on the substitutions to the Ar group may be described as enriched in one stereo configuration or racemic.

The following structures are intended as representative examples of chemical agents described herein but should not be construed as limiting this example beyond that described above.

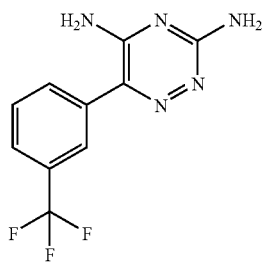

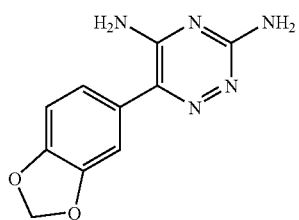

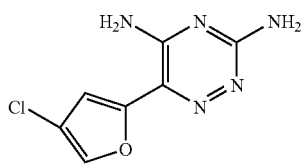

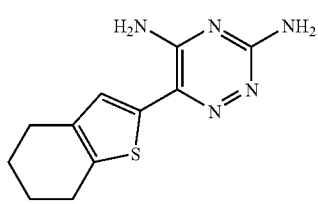

Example 9

As a further embodiment of Example 1, we propose the class of organic molecules and their pharmaceutically acceptable salts wherein they may be described by the following schematic diagram:

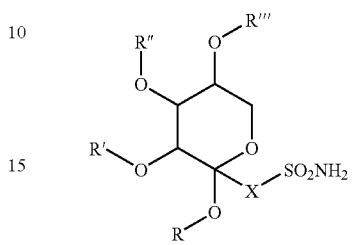

Within the context of this embodiment of the example, X may be described as being an aliphatic or heteroaliphatic group. Preferred within this example are X groups that are made up of 1-4 atoms, which may be composed of —$CH_2$—, —O— or —NH— groups. As an example of the types of groups embodied herein, X may be described as being selected from but not limited to the following groups: —$CH_2$—; —$(CH_2)_2$—; —$(CH_2)_3$—; —$(CH_2)_4$—; —$CH_2O$—, —$OCH_2$—, —$CH_2NH$—; —$(CH_2)_2O$—; —$(CH_2)_2NH$—. Within the further context of this example, R, R', R", R'" may described as being proton, aliphatic or heteroaliphatic. As an example of the types of groups preferred herein, R, R', R" and R'" may individually be described as being a selected from but not limited to the following groups: H—; $CH_3$—; $CH_3CH_2$—; $CH_3CH_2CH_2$—; $CH(CH_3)_2$—. Additionally, R and R', as well as R" and R'" may fused, so as to form a cyclic acetal, or ketal, and as an example of the types of groups preferred herein, —R—R'— and —R"—R'"— may individually be described as being from but not limited to the following list: —$CH_2$—; —CH($CH_3$)—, —$C(CH_3)_2$—. In this embodiment of the example, R, R', R", R'" may be independently composed of the above described components, and may be identical or non-identical. The glycoside core of the molecule can be chiral, and composed of a single enantiomer, racemic or a mixture of steromeric epimers, particularly with respect to the anomeric carbon.

The following structures are intended as representative examples of chemical agents described herein but should not be construed as limiting this example beyond that described above.

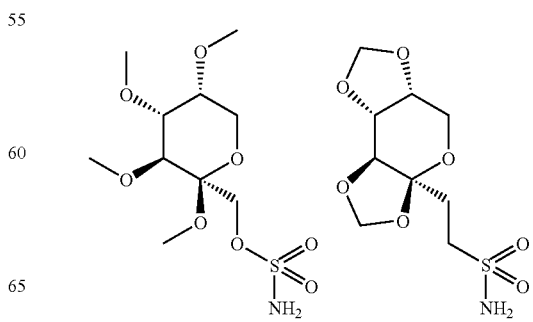

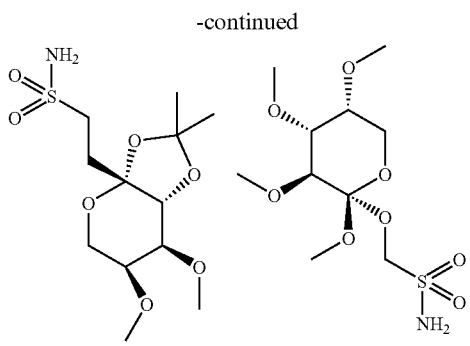

Example 10

As a further embodiment of Example 1, we propose the class of organic molecules and their pharmaceutically acceptable salts wherein they may be described by the following schematic diagram:

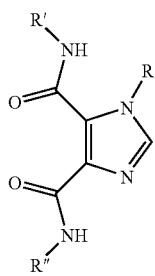

Within the context of this manifestation of the example, R, R' and R" can be individually described as being proton, aliphatic, heteroaliphatic, aromatic, heteroaromatic, aliphatic-aromatic or aliphatic-heteroaromatic. Additionally, R and R' may be fused so as to form a heterobicyclic structure. Such a bridging group may be described as being aliphatic or heteroaliphatic, and may be comprised of a chain containing one, two or three atoms in length. The groups comprising R, R' and R" may also contain additional stereocenters, where the resulting molecule may be described as being enriched in a single enantiomer or racemic.

The following structures are intended as representative examples of chemical agents described herein but should not be construed as limiting this example beyond that described above.

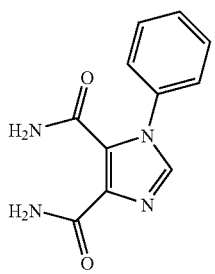

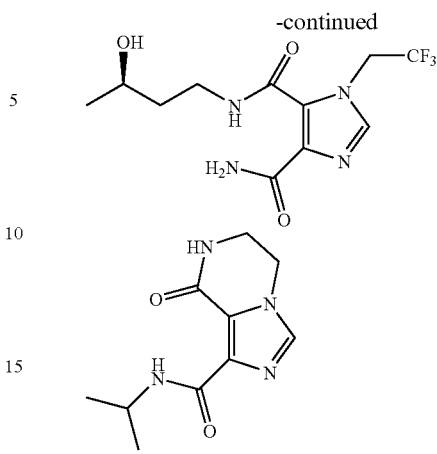

Example 11

One aspect of this example may be described as being the means of selecting chemical agents from those as embodied in Examples 1-10 on the basis of their ability to inhibit AQP4 mediated water transport as indicated by an in vitro functional assay.

Example 12

One aspect of this example may be described as being the means of selecting chemical agents such as those embodied in Examples 1-10 on the basis of their ability to selectively bind to the AQP4 protein as indicated by an in vitro binding assay.

Example 13

One aspect of this example can be embodied by the means of selecting chemical agents on the basis of their having a comparable or superior docking energy or docking score with the AQP4 protein monomer as indicated by an in silico virtual screening or docking study, as compared to AQP4 inhibitory molecules as selected from those described in Examples 1-10.

Example 14

One aspect of this example may be described as being the means of selecting chemical agents on the basis of their having similar physiochemical properties as AQP4 inhibitors selected from those preferred in Examples 1-10. The similarities in the physicochemical properties can be analyzed by comparing explicit 2D- or 3D-descriptors or by using a genetic algorithm, whereby the physiochemical terms used for the comparison are not defined explicitly.

Example 15

One aspect of this example may be described as being the means of synthesizing individual AQP4 inhibitory compounds as described in Examples 1-10, or those identified in Examples 11-14 or a combination thereof, using means that are known to practitioners of normal skill in the art.

Example 16

One aspect of this example can be embodied by the means of using the AQP4 inhibitors described or identified in examples 1-14 as medicants for the treatment of human disease. These AQP4 inhibitory molecules can be utilized individually, or as a constitutive part of a polytherapy or drug-cocktail treatment. When used in a polytherapy treatment, the AQP4 inhibitory agent can be either utilized as an individual component combined with other pharmaceutically active agents, where each interact with a separate drug target, or alternatively as a single chemical agent that interacts preferentially with two or more drug targets, where one mode of action is the inhibition of AQP4 function, as would be known to practitioners of normal skill in the art.

Example 17

One aspect of this example may be described as being the physical form and means of administering the AQP4 inhibitory compounds as described or identified in examples 1-14. These physical forms may be described as being solid, liquid or gaseous, wherein the active component can be compounded with other active or inactive components, such as to achieve the desired physical format and pharmacological properties as would be known to practitioners of normal skill in the art.

Example 18

One aspect of this example can be embodied by the application of AQP4 inhibitory molecules as described or identified in examples 1-14 as therapeutic agents for the prevention, prophylaxis and treatment of disease pathology directly or indirectly related to AQP4 function.

Example 19

As a further embodiment of that described in Example 18, one aspect of this example may be described as being the use of AQP4 inhibitory molecules as described or identified in examples 1-14 in the treatment and prophylaxis of cerebral edema and the pathologies related thereto as would be understood by practitioners of normal skill in the art.

Example 20

As a further embodiment of that described in Example 18, one aspect of this example may be described as being the use of AQP4 inhibitory molecules as described or identified in examples 1-14 in the prevention and prophylaxis of ischemia and ischemic injury as would be understood by a practitioner of normal skill in the art.

Example 21

As a further embodiment of that described in Example 18, one aspect of this example may be described as being the use of AQP4 inhibitory molecules as described or identified in examples 1-14 in the treatment of encephalitis and diseases related thereto.

Example 22

As a further embodiment of that described in Example 18, one aspect of this example may be described as being the use of AQP4 inhibitory molecules as described or identified in examples 1-14 in the treatment and prophylaxis of neurological disease and the pathologies related thereto as would be understood by a practitioner of normal skill in the art.

Example 23

As a further embodiment of that described in Example 22, one aspect of this example may be described as being the use of AQP4 inhibitory molecules as described or identified in examples 1-14 in the prophylaxis of epilepsy, seizure and involuntary convulsive disorders related thereto as would be understood by a practitioner of normal skill in the art.

Example 24

As a further embodiment of that described in Example 22, one aspect of this example may be described as being the use of AQP4 inhibitory molecules as described or identified in examples 1-14 in the treatment and prophylaxis of bipolar disorder and psychological diseases related thereto as would be understood by a practitioner of normal skill in the art.

Example 25

As a further embodiment of that described in Example 22, one aspect of this example may be described as being the use of AQP4 inhibitory molecules as described or identified in examples 1-14 in the treatment and prophylaxis of schizophrenia and psychological diseases related thereto as would be understood by a practitioner of normal skill in the art.

Example 26

As a further embodiment of that described in Example 22, one aspect of this example may be described as being the use of AQP4 inhibitory molecules as described or identified in examples 1-14 in the treatment and prophylaxis of restless leg syndrome and diseases related thereto as would be understood by a practitioner of normal skill in the art.

Example 27

As a further embodiment of that described in Example 22, one aspect of this example may be described as being the use of AQP4 inhibitory molecules as described or identified in examples 1-14 in the treatment and prophylaxis of diabetic neuropathy and morbidity related thereto as would be understood by a practitioner of normal skill in the art.

Example 28

As a further embodiment of that described in Example 22, one aspect of this example may be described as being the use of AQP4 inhibitory molecules as described or identified in examples 1-14 in the treatment and prophylaxis of dystonia and disorders related thereto as would be understood by a practitioner of normal skill in the art.

Example 29

As a further embodiment of that described in Example 22, one aspect of this example may be described as being the use of AQP4 inhibitory molecules as described or identified in examples 1-14 in the treatment of Huntington's disease as would be understood by a practitioner of normal skill in the art.

Example 30

As a further embodiment of that described in Example 22, one aspect of this example may be described as being the use of AQP4 inhibitory molecules as described or identified in examples 1-14 in the treatment and prophylaxis of Parkinson's disease and the morbidity related thereto as would be understood by a practitioner of normal skill in the art.

Example 31

As a further embodiment of that described in Example 18, one aspect of this example may be described as being the use of AQP4 inhibitory molecules as described or identified in examples 1-14 in the treatment and prophylaxis of migraine and pain disorders related thereto as would be understood by a practitioner of normal skill in the art.

Example 32

As a further embodiment of that described in Example 18, one aspect of this example may be described as being the use of AQP4 inhibitory molecules as described or identified in examples 1-14 in the treatment and prophylaxis of dementia as would be understood by a practitioner of normal skill in the art.

Example 33

As a further embodiment of that described in Example 18, one aspect of this example may be described as being the use of AQP4 inhibitory molecules as described or identified in examples 1-14 in the treatment of drug addition as would be understood by a practitioner of normal skill in the art.

Example 34

As a further embodiment of that described in Example 18, one aspect of this example may be described as being the use of AQP4 inhibitory molecules as described or identified in examples 1-14 in the treatment and prophylaxis of ocular disease and the pathologies related thereto as would be understood by a practitioner of normal skill in the art.

Example 35

As a further embodiment of that described in Example 34, one aspect of this example may be described as being the use of AQP4 inhibitory molecules as described or identified in examples 1-14 in the prevention and prophylaxis of retinal ischemia as would be understood by a practitioner of normal skill in the art.

Example 36

As a further embodiment of that described in Example 34, one aspect of this example may be described as being the use of AQP4 inhibitory molecules as described or identified in examples 1-14 in the treatment and prophylaxis of glaucoma as would be understood by a practitioner of normal skill in the art.

Example 37

As a further embodiment of that described in Example 34, one aspect of this example may be described as being the use of AQP4 inhibitory molecules as described or identified in examples 1-14 in the treatment of proliferative retinopathy and pathology related thereto as would be understood by a practitioner of normal skill in the art.

Example 38

As a further embodiment of that described in Example 34, one aspect of this example may be described as being the use of AQP4 inhibitory molecules as described or identified in examples 1-14 in the treatment of bullous keratopathy and complications thereof as would be understood by a practitioner of normal skill in the art.

Example 39

As a further embodiment of that described in Example 18, one aspect of this example may be described as being the use of AQP4 inhibitory molecules as described or identified in examples 1-14 in the treatment of tumors and cancerous growths and morbidity related thereto as would be understood by a practitioner of normal skill in the art.

Example 40

As a further embodiment of that described in Example 18, one aspect of this example may be described as being the use of AQP4 inhibitory molecules as described or identified in examples 1-14 in the treatment and prophylaxis of Meniere's disease and pathology related thereto as would be understood by a practitioner of normal skill in the art.

Bio-Assay

Compounds studied in vitro were purchased from Sigma-Aldrich, Tokyo Kasei, Wako or Scientific Exchange, and were used without further purification. In all cases the compounds provided were in excess of 97% purity. Compound samples were freshly dissolved into DMSO (Sigma, Hibri-Max) and diluted into RO deionized water (Milipore, Ultra-Q) prior to use. Other reagents were purchased from Sigma and Wako and were used without modification. Modified Barth's Medium (MBS) and isolation buffer were prepared using autoclaved, doubly distilled water. MBS was used for up to one week after its preparation. MBS was prepared to contain NaCl (88 mM), KCl (1 mM), HEPES (10 mM), $MgSO_4$ (0.82 mM), $NaHCO_3$ (2.4 mM), $CaCl_2$ (0.91 mM), $Ca(NO_3)_2$ (0.33 mM) and gentamicin (100 mg/L), at a pH=7.5. Isolation buffer was prepared to contain NaCl (108 mM), KCl (2 mM), EDTA, (2 mM), HEPES (10 mM), and was at pH=7.5.

cDNA encoding human aquaporin-4 M23 isoform (hAQP4b) was cloned by reverse-transcription polymerase chain reaction (RT-PCR). First-strand cDNA was synthesized from human cerebellum total RNA by using the Advantage RT-for-PCR Kit (CLONTECH). The following oligonucleotide PCR primers were designed based on published hAQP4b sequences (Lu, et al. *Proc. Nat. Acad. Sci. USA* 1996, 93, 10908): forward 5'-CAGTAAGTGTGGAC-CTTTGT-3', reverse 5'-TCATACTGAAGACAATACCT-3'. Full-length cRNA was subcloned into pSP35T expression vector for *Xenopus* oocytes (Amaya, et al. *Cell* 1991, 66, 257). The resulting cRNA was sequenced using an Applied Biosystems PRISM 3100 genetic analyzer, and was in agreement with literature reports (Lu, et al. *Proc. Nat. Acad. Sci. USA* 1996, 93, 10908). The hAQP4b specific cRNA was stored at −80° C. as a microdispersion in 67% aqueous ethanol containing 0.1 mM NaOAc (total AQP4 cRNA concentration=1 μg/20 μL).

Oocytes from an adult, female *Xenopus laevis* were transferred portion-wise to a Petri dish containing isolation buffer, where the follicular membranes and vitelline were removed manually, thereby yielding denuded oocytes (Sakimura, et al. *FEBS Lett.* 1990, 272, 73). Denuded stage V-VI oocytes were then returned to fresh MBS medium and allowed to equilibrate for a minimum of 2 h at 18° C. prior to cRNA injection. Denuded oocytes unused after 24 h were discarded. An aliquot of hAQP4b cRNA solution (20 μL) was pelleted by centrifugation (15,000 rpm, 14 min, 4° C.), the pellet was washed sequentially with 70% aqueous ethanol, then 100% ethanol (centrifugation between washes at 15,000 rpm, 3 min, 4° C.), air dried, and finally reconstituted in distilled water (10 µL). An aliquot (30 nL) of either the resulting 0.1 µg/µL cRNA solution (3 ng hAQP4b cRNA/oocyte) or distilled water (sham) was injected into each oocyte using a Drummond oocyte injection system. The injected oocytes were then incubated for 48 h at 18° C. in MBS. The medium was changed and non-viable oocytes removed 24 and 48 h post injection.

An oocyte assay procedure was developed as follows: At a minimum of 3 h prior to the assay, oocytes were transferred to a 96 well microplate (Falcon 353077) along with 45 µL of MBS. An aliquot of a 200 µM inhibitor solution (5 µL, 1% aq. DMSO), or blank (5 µL, 1% aq. DMSO) was introduced to the oocyte containing well 2 h before the assay. The final concentration of the incubation medium was 20 µM in inhibitor with 0.1% DMSO. A secondary plate was likewise prepared by diluting an aliquot of the 200 µM inhibitor solution (15 µL, 1% aq. DMSO) or blank (15 µL, 1% aq. DMSO) with distilled water (135 µL). The assay was performed by transferring an aliquot of the secondary plate medium (100 µL) to the corresponding well on the incubation plate. The oocyte expansion was monitored using an Olympus SZX12 microscope connected to a Nikon DSL1 digital imaging system, with a nominal magnification factor of 20×. The initial image (nominally t=3 s) and subsequent images (60 s intervals) were recorded for up to 4 minutes post dilution.

Images were transferred to a PC and the area of each oocyte was evaluated using NIH Image-J. The cross-sectional area values for each oocyte at time=t were converted to volumes assuming a spherical relationship. The relative volume of each oocyte compared to its initial volume was then determined. Relative oocyte volumes were then averaged for n oocytes along with the standard error at each point. The percent inhibition (% inh) of AQP4 mediated hypoosmotic expansion was given by the relationship % inh=100(1−{[(Pf±SE)−(Pf$_{sham}$±SE$_{sham}$)]/[(Pf$_{blank}$±SE$_{blank}$)−(Pf$_{sham}$±SE$_{sham}$)]}), where Pf±SE represents the average osmotic permeability of n AQP4 injected oocytes and their standard error at each inhibitor concentration, Pf$_{sham}$±SE$_{sham}$ is similarly the osmotic water permeability of the water injected oocytes, and Pf$_{blank}$±SE$_{blank}$ is that of the AQP4 cRNA injected oocytes incubated with a blank solution. The osmotic water permeability (Pf) of each oocyte was determined from the rates of the oocyte expansion given by $d(V/V_0)/dt$ according to the relationship, Pf=[$V_o$×d(V/V$_0$)/dt]/[S×V$_w$×(osm$_{in}$−osm$_{out}$)], where the initial oocyte volume $V_o$=9×10$^{-5}$, the initial oocyte surface area S=0.0045 cm$^2$, the molar volume of water V$_w$=18 cm$^3$/mol, inner oocyte osmolarity osm$_{in}$=200 mOsM, and outer oocyte osmolarity osm$_{out}$=67 mOsM (Brooks, et al. *Molec. Pharmacol.* 2000, 57, 1021). Data was evaluated using a single tail ANOVA, P-values less than 0.05 indicate statistical significance.

The dose response analysis was performed as described above; however the concentration of ligand in both the assay and incubation media were adjusted to 0.1, 1, 5, 10, 20 and 100 µM for n=5 oocytes. Samples were specifically prepared, such that the final DMSO concentration in each assay well was fixed at 0.1% at all concentrations of ligand and the blank solutions. Apparent IC$_{50}$ values were calculated from the inhibition values derived from the dose response data using a sigmoidal function.

Virtual Assay

A protein monomer taken from the rat aquaporin-4 M23 (rAQP4b) electron diffraction structure (2D57) (Hiroaki, et al. *J. Mol. Bio.* 2006, 355, 628) was imported into the BioMedCAChe molecular modeling environment (Fujitsu Ltd, version 6.1.12.34). The imported protein structure was corrected for valence, atom type and charge. Active site residues were selected primarily from the mouth region of the water channel, including residues Val-53, Ile-56, Trp-59, Asp-69, Phe-77, Gly-143, Gly-146, Val-147, Ile-148, Ile-149, His-151, His-201, Ile-205, Gly-209, Ala-210 and Asp-216. The ligand used for the docking simulation was defined using all of the substrate's atoms, whose structure was independently optimized using a combination of MM3, MM3/Conflex and PM5 methods. The ligand docking was then completed using the Active Site module within BioMedCache and the included PMF energy function. The active site residue side-chains and ligand were allowed to be flexible during the minimization, while the remainder of the protein atom coordinates were fixed. The final docking energy was reported in Kcal/mol and did not include ligand van der Waals terms.

Table 1 represents the results of in silico studies to identify what structural features are needed for binding to the extracellular domain of the AQP4 trans-membrane protein. The column titled DE represents the binding energy determined for each of 20 respective compounds, and is reported in the units Kcal/mol.

TABLE 1

| Compound | DE (Kcal/mol) |
| --- | --- |
| 1 | −63.666 |
| 2 | −70.711 |
| 3 | −67.042 |
| 4 | −53.963 |
| 5 | −63.656 |
| 6 | −33.363 |
| 7 | −57.455 |
| 8 | −57.980 |
| 9 | −66.896 |
| 10 | −55.606 |
| 11 | −66.101 |
| 12 | −62.726 |
| 13 | −68.872 |
| 14 | −63.726 |
| 15 | −69.440 |
| 16 | −69.710 |
| 17 | −64.452 |
| 18 | −63.672 |
| 19 | −64.844 |
| 20 | −56.803 |

Explanation on Abbreviations Used

TABLE 2

Graphical description of the Ar groups described in the invention

| Abbreviation | Structure |
| --- | --- |
| 4-substituted benzene-1-sulfonamide | ◆—⟨benzene⟩—S(=O)(=O)NH$_2$ |
| 5-substituted pyridine-2-sulfonamide | ◆—⟨pyridine⟩—S(=O)(=O)NH$_2$ |

TABLE 2-continued

Graphical description of the Ar groups described in the invention

| Abbreviation | Structure |
|---|---|
| 2-substituted pyrazine-5-sulfonamide | 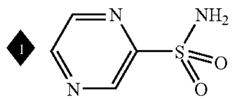 |
| 5-substituted pyrimidine-2-sulfonamide | 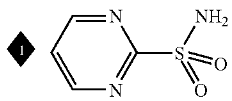 |
| 5-substituted oxazole-2-sulfonamide | 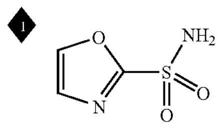 |
| 5-substituted thiaziazole-2-sulfonamide | 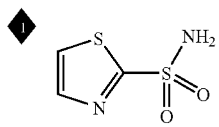 |
| 2-substituted oxadiazole-5-sulfonamide | 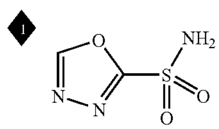 |
| 2-substituted thiazole-5-sulfonamide | 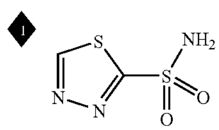 |
| 2-substituted imidizole-4-sulfonamide | 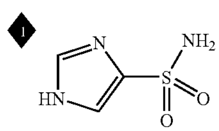 |
| 1-substituted diazole-3-sulfonamide | 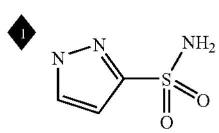 |
| 5-substituted benzothiazole-2-sulfonamide | 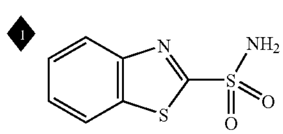 |
| 6-substituted benzothiazole-2-sulfonamide | 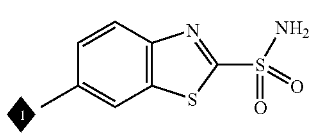 |
| 5-substituted benzoxazole-2-sulfonamide | 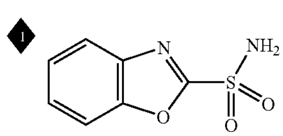 |
| 6-substituted benzoxazole-2-sulfonamide | |
| 3-substituted pyridine | |
| 2-substituted pyrazine | |
| 5-substituted pyrimidine | |
| 5-substituted oxazole | |
| 2-substituted thiadiazole | |
| 2-substituted oxadiazole | |
| 5-substituted thiazole | |
| 5-substituted imidizole | |
| 1-substituted imidazole | |
| 5-substituted diazole | |

TABLE 2-continued

Graphical description of the Ar groups described in the invention

| Abbreviation | Structure |
|---|---|
| 4-substituted isothiazole | 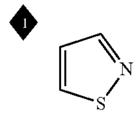 |
| 5-substituted isothiazole | 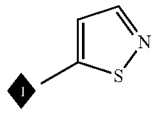 |
| 4-substituted isoxazole | 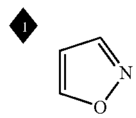 |
| 5-substituted isoxazole | 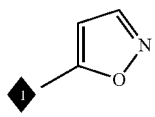 |
| 5-substituted benzothiazole | 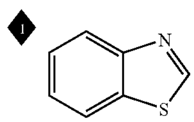 |
| 6-substituted benzothiazole | 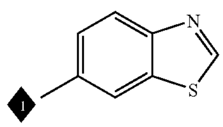 |
| 5-substituted benzoxazole | 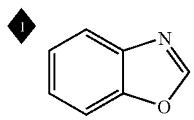 |
| 6-substituted benzoxazole | 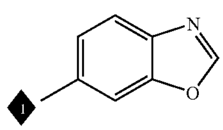 |
| 5-sunstituted benzimidazole | 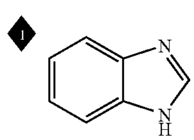 |
| 6-substituted cinnoline | 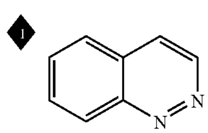 |
| 7-substituted cinnoline | 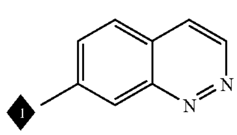 |
| 6-substituted quinoxaline | 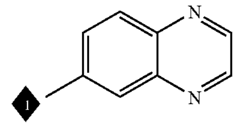 |
| 6-substituted quinazoline | 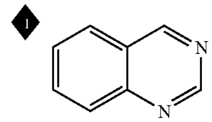 |
| 7-substituted quinazoline | 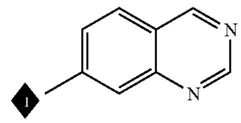 |
| 6-substituted napthyridin | 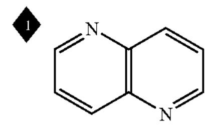 |
| 7-substituted napthyridine | |
| 7-substituted napthyridine | |
| 2-substituted napthyridine | 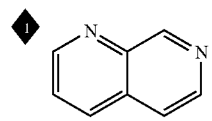 |

SIGNIFICANCE OF THE INVENTION

Within the context of the invention described herein, "Aquaporin 4", and thereby its abbreviation, "AQP4", can be taken to mean the human Aquaporin 4 isozyme. Included in this description of AQP4 is its long form, generally referred to as Aquaporin 4-M1, and also its short from, generally referred to as Aquaporin 4-M23. Within the context of in vivo, ex vivo, in vitro and particularly in silico studies, the term "Aquaporin 4" and thereby its abbreviation, "AQP4" can refer to the isozymes of that protein of non-human origin.

The present invention relates to the identification of molecular inhibitors of AQP4, the means of identifying such compounds, and their applications thereof. This invention has a wide range of implications for pharmaceutical and medical applications, since molecular agents identified in this invention can be used as medicants for the treatment of human disease. Moreover, the compounds identified herein can also be used in in vivo, in vitro and in silico applications to identify new inhibitors of AQP4 that have physiological properties suitable for pharmacological uses. The molecular entities identified as AQP4 inhibitors during the course of this invention include known pharmaceutical agents, as well as organic molecules whose pharmaceutical properties are unknown. A representative summary of inhibitors identified for AQP4, their docking energy and in vitro inhibitory activity are described in Table 3.

TABLE 3

Representative AQP4 inhibitors identified by this invention.

| entry | structure | systematic name | $DE_{dock}{}^a$ | % Inh$^b$ | $IC_{50}{}^c$ |
|---|---|---|---|---|---|
| 1 | 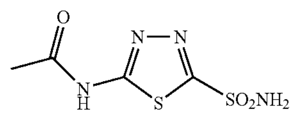 | N-(5-sulfamoyl-1,3,4-thiadiazol-2-yl)acetamide | −63.666 | 78 ± 3 | 0.86 (86) |
| 2 | 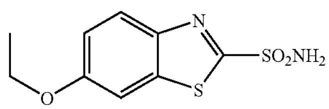 | 6-ethoxybenzo[d]thiazole-2-sulfonamide | −67.042 | 66 ± 4 | d |
| 3 | 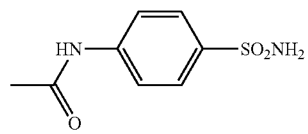 | N-(4-sulfamoylphenyl)acetamide | −53.963 | 23 ± 5 | d |
| 4 | 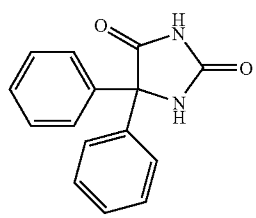 | 5,5-diphenylimidazolidine-2,4-dione | −51.432 | 58 ± 4 | 9.8 (60) |
| 5 | 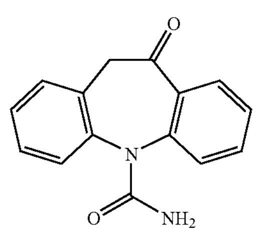 | 10-oxo-10,11-dihydro-5H-dibenzo[b,f]azepine-5-carboxamide | −47.890 | 33 ± 4 | d |
| 6 | 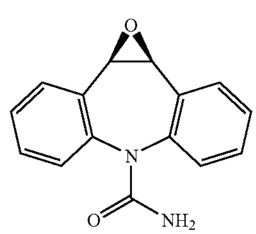 | (1aR, 10bS)-1aH-dibenzo[b,f]oxireno[2,3-d]azepine-6(10bH)-carboxamide | −50.231 | 40 ± 7 | d |
| 7 | 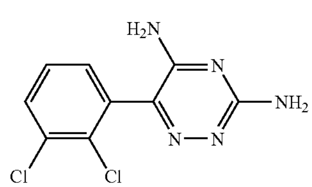 | 6-(2,3-dichlorophenyl)-1,2,4-triazine-3,5-diamine | −63.656 | 54 ± 9 | 8.1 (64) |

TABLE 3-continued

Representative AQP4 inhibitors identified by this invention.

| entry | structure | systematic name | DE$_{dock}$[a] | % Inh[b] | IC$_{50}$[c] |
|---|---|---|---|---|---|
| 8 | 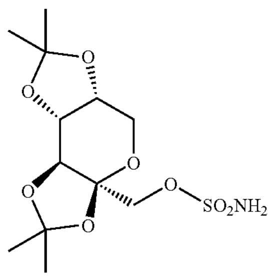 | ((3aS,5aR,8aR,8bS)-2,2,7,7-tetra-methyltetrahydro-3aH-bis[1,3]dioxolo[4,5-b:4',5'-d]pyran-3a-yl)methyl sulfamate | −70.710 | 67 ± 6 | 10.1 (75) |
| 9 | 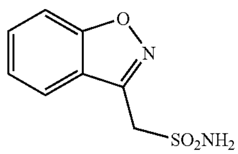 | benzo[d]isoxazol-3-ylmethane sulfonamide | −47.498 | 19 ± 5 | d |
| 10 | 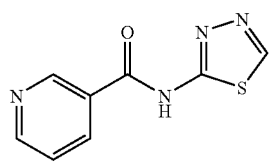 | N-(1,3,4-thiadiazol-2-yl)nicotinamide | −62.776 | 67 ± 6 | 3.1 (73) |
| 11 | 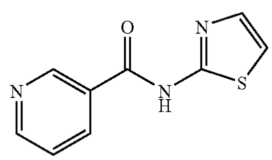 | N-(thiazol-2-yl)nicotinamide | −58.110 | 21 ± 7 | 3.4 (23) |
| 12 | 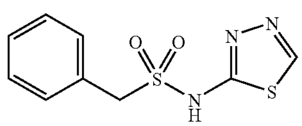 | 1-phenyl-N-(1,3,4-thiadiazol-2-yl)methanesulfonamide | −58.345 | 45 ± 8 | d |
| 13 | 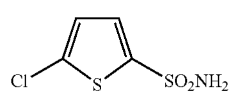 | 2-chlorothiophene-5-sulfonamide | −40.003 | 18 ± 9 | d |
| 14 | 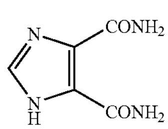 | 1H-imidazole-4,5-dicarboxamide | −47.941 | 23 ± 8 | d |
| 15 | 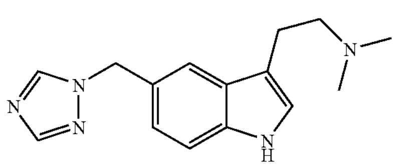 | 2-(5-((1H-1,2,4-triazol-1-yl)methyl)-1H-indol-3-yl)-N,N-dimethylethanamine | −71.035 | 51 ± 5 | 2.9 (54) |

Notes for Table 3
(a) Docking score determined for each compound and rAQP4b in Kcal/mol.
(b) Percent inhibition (% Inh) and cumulated error determined for the listed compounds at [X]=20 μM. P<0.05
(c) IC$_{50}$ values (μM) and (IA$_{max}$) for the listed compounds determined from inhibitory data at 0.01≦[X]≦100 μM.
(d) Not completed.

TABLE 4

Representative compounds identified by this invention lacking AQP4 inhibitory activity.

| entry | structure | systematic name | $DE_{dock}$[a] | % Inh[b] |
|---|---|---|---|---|
| 1 | 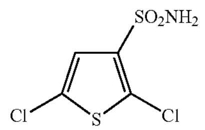 | 2,5-dichlorothiophene-3-sulfonamide | −34.186 | c |
| 2 | 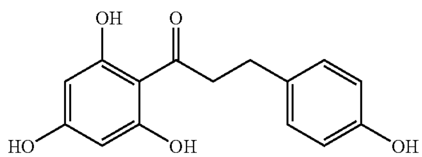 | 3-(4-hydroxyphenyl)-1-(2,4,6-trihydroxyphenyl)propan-1-one | −62.293 | c |
| 3 | 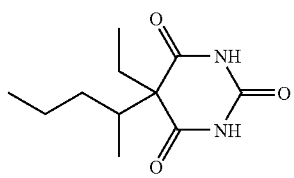 | 5-ethyl-5(pentan-2-yl)pyrimidine-2,4,6(1H,3H,5H)-trione | −45.848 | c |
| 4 | 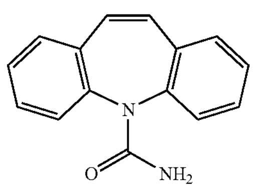 | (Z)-5H-dibenzo[b,f]azepine-5-carboxamide | −45.045 | c |
| 5 | 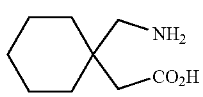 | 2-(1-(aminomethyl)cyclohexyl) acetic acid | −39.005 | c |
| 6 | 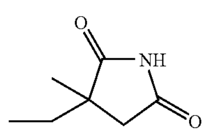 | 3-ethyl-3-methylpyrrolidine-2,5-dione | −33.468 | c |

Notes for Table 4
(a) Docking score determined for each compound and rAQP4b in Kcal/mol.
(b) Percent inhibition (% Inh) and cumulated error determined for the listed compounds at [X]=20 μM. P<0.05
(c) No statistically relevant inhibition in AQP4 function was observed.

In the course of the invention described in this report, an in vitro assay was developed that allowed the ability of a compound to inhibit AQP4 mediated water transport to be determined based on its ability reduce the hypotonic swelling of *Xenopus laevis* ooctes that have been transfected such that they express the AQP4 protein, specifically the human Aquaporin 4-M23 isozyme. The maximum volume, rate of change and sensitivity of the transfected oocytes to decreased contacting medium osmolarity, both in the absence or presence of a chemical agent were compared to determine the overall effect of that chemical on AQP4 mediated water transport. Compounds that were identified as having an inhibitory effect on AQP4 mediated water transport were shown to reduce the rate of hypotonic oocyte swelling between those oocytes contacted incubated with a chemical compound and those identically prepared with a blank in a statistically significant manner, wherein statistical analysis indicated a P<0.05 between the data sets described herein. Compounds were analyzed more than two times using oocytes from different *Xenopus laevis* as a means of ensuring the observed effect was not a result of the individual oocytes or their preparation.

Oocytes showing an AQP4 inhibitory effect at a single dose, typically 20 μM, were assayed in varying concentrations to assess the dose dependency of their effect. Typically, this dose dependency was evaluated using more than 5 data points in a concentration range greater than 2 orders of magnitude. Within the context of this invention, the term dose dependent described the situation wherein a change in the concentration of the contacting inhibitor leads to a concomitant change in the rate of hypotonic oocyte swelling. As such, an observed dose dependency can be used as an additional test to the consistency of the assay model. In the context of the invention described herein, dose dependent behavior was observed for compounds of different structural subtypes which further increased the likelihood that the AQP4 inhibitory activity was related to the behavior of that specific compound.

Figure 8:
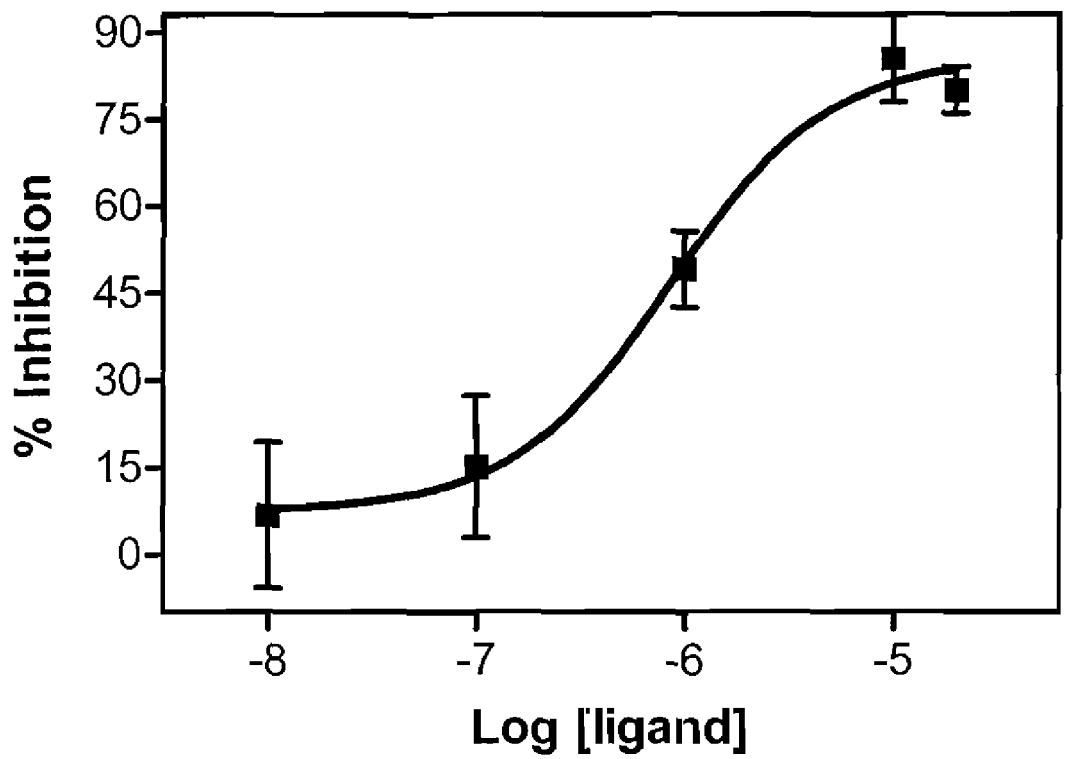
FIG. 8 is a graph showing dose dependent inhibition of AQP4 by N-(5-sulfamoyl-1,3,4-thiadiazol-2-yl)acetamide. Solid points represent the percent inhibition of AQP4 mediated water transport at that respective concentration of ligand, error bars represent the total standard error for that point, solid line represents the non-linear least squares fit of the data. $IC_{50}$=0.86 µM.

In the course of the invention described in this report, organic chemical entities that can collectively be described as being an aryl sulfonamide were fount to be capable of inhibiting AQP4 mediated water transport. These chemical entities were typified by N-(5-sulfamoyl-1,3,4-thiadiazol-2-yl)acetamide (FIG. 8). Among this class of aromatic sulfonamide based AQP4 inhibitors were those that are known therapeutic agents used in the treatment of epilepsy, migraine, anxiety disorders, depression, schizophrenia, bipolar disorder, cerebral edema, acute altitude sickness, glaucoma, Meniere's disease, and some symptoms related to Marfan syndrome.

Figure 9:
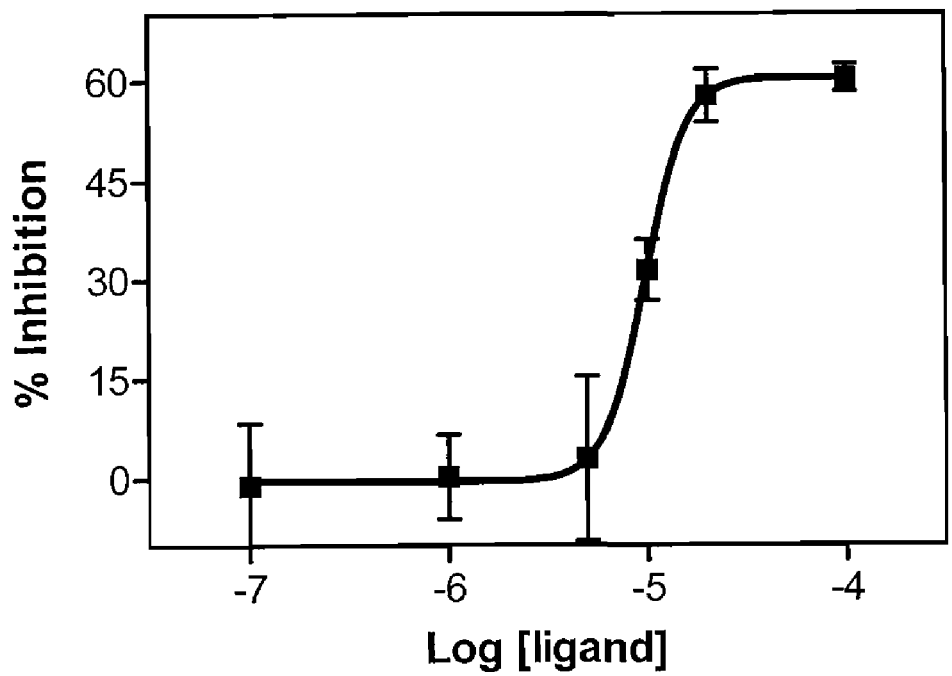
FIG. 9 is a graph showing dose dependent inhibition of AQP4 by 5,5-diphenylimidazolidine-2,4-dione. Solid points represent the percent inhibition of AQP4 mediated water transport at that respective concentration of ligand, error bars represent the total standard error for that point, solid line represents the non-linear least squares fit of the data. $IC_{50}$=9.8 µM.

Also in the course of this invention, organic chemical entities that may be described as principally being a bi-aryl compounds were found to be capable of inhibiting AQP4 mediated water transport. These bi-aryl chemical agents were typified by 5,5-diphenylimidazolidine-2,4-dione (FIG. 9). Included in this class AQP4 inhibitory compounds are those known to have anti-convulsant, anti-depressant, anti-anxiolitic, anti-ischemic and analgesic properties, and that are also used in the treatment and prophylaxis of bipolar disorder, schizophrenia and Huntington's disease.

Figure 10:
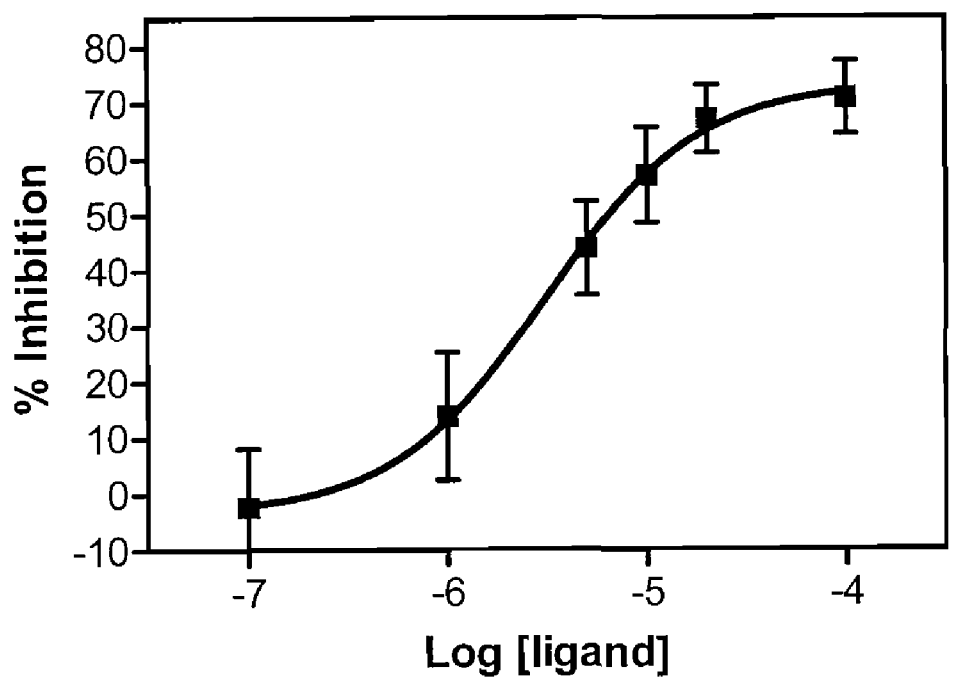
FIG. 10 is a graph showing dose dependent inhibition of AQP4 by N-(1,3,4-thiadiazol-2-yl)nicotinamide. Solid points represent the percent inhibition of AQP4 mediated water transport at that respective concentration of ligand, error bars represent the total standard error for that point, solid line represents the non-linear least squares fit of the data. $IC_{50}$=3.1 µM.

Also in the course of this invention, organic chemical entities that may be described as being thiadiazole containing compounds were found to be capable of inhibiting AQP4 mediated water transport. These thiadiazole compounds can be typified by N-(1,3,4-thiadiazol-2-yl)nicotinamide (FIG. 10).

Figure 11:
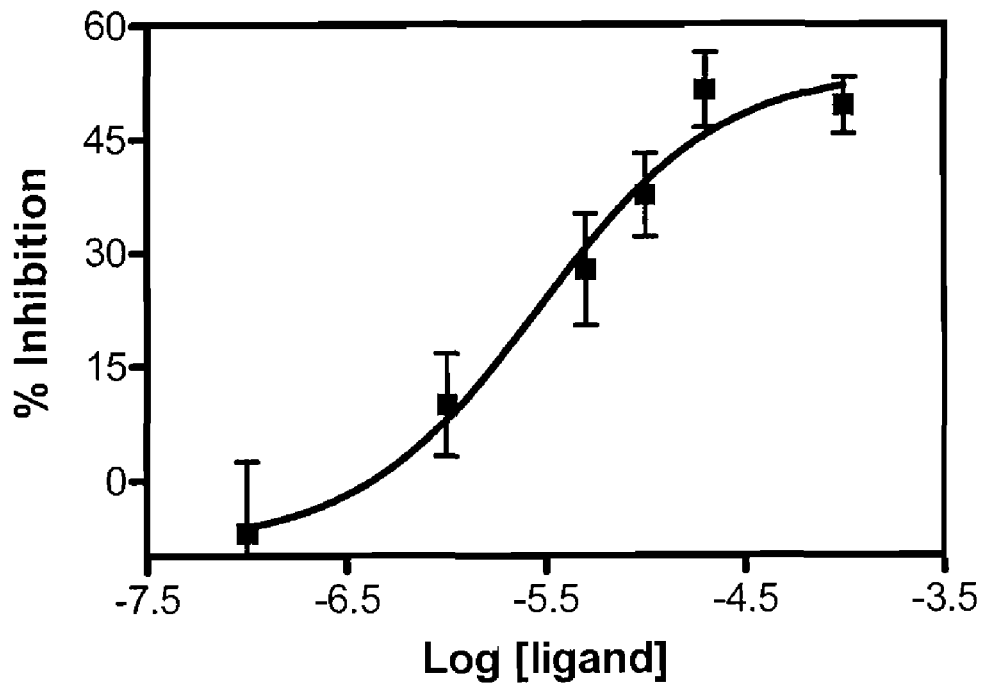
FIG. 11 is a graph showing dose dependent inhibition of AQP4 by 2-(5-((1H-1,2,4-triazol-1-yl)methyl)-1H-indol-3-yl)-N,N-dimethylethanamine. Solid points represent the percent inhibition of AQP4 mediated water transport at that respective concentration of ligand, error bars represent the total standard error for that point, solid line represents the non-linear least squares fit of the data. $IC_{50}$=2.9 µM.

Also in the course of this invention, organic chemical entities that may be described as being triazole containing compounds were found to be capable of inhibiting AQP4 mediated water transport. These triazole containing chemical agents can be typified by 2-(5-((1H-1,2,4-triazol-1-yl)methyl)-1H-indol-3-yl)-N,N-dimethylethanamine (FIG. 11). Included in this class of AQP4 inhibitory compounds are those known to have anti-convulsant, analgesic and vasodialatory properties.

Figure 12:
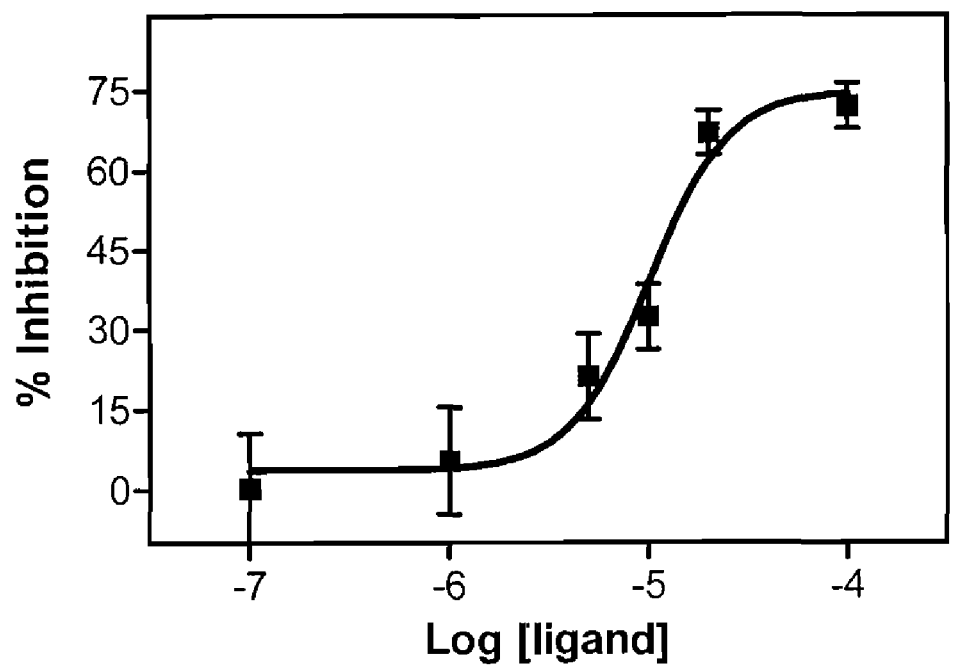
FIG. 12 is a graph showing dose dependent inhibition of AQP4 by ((3aS,5aR,8aR,8bS)-2,2,7,7-tetramethyltetrahydro-3aH-bis[1,3]dioxolo[4,5-b: 4',5'-d]pyran-3a-yl)methyl sulfamate. Solid points represent the percent inhibition of AQP4 mediated water transport at that respective concentration of ligand, error bars represent the total standard error for that point, solid line represents the non-linear least squares fit of the data. $IC_{50}$=10.1 µM.

Also in the course of this invention, organic chemical entities that may be described as being sulfamate functionalized monosaccharides were found to be capable of inhibiting AQP4 mediated water transport. These sulfamate monosaccaride based chemical agents can be typified by ((3aS,5aR,8aR,8bS)-2,2,7,7-tetramethyltetrahydro-3aH-bis[1,3]dioxolo[4,5-b: 4',5'-d]pyran-3a-yl)methyl sulfamate (FIG. 12). Included in this class of AQP4 inhibitory compounds are those know to have anti-convulsant and analgesic properties.

Also identified in the course of this invention, chemical entities that may be described as being imidazole bis-amides were found to be capable of inhibiting AQP4 mediated water transport. These imidazole bis-amide based chemical entities can be typified by 1H-imidazole-4,5-dicarboxamide (Table 3, entry 13).

Figure 13:
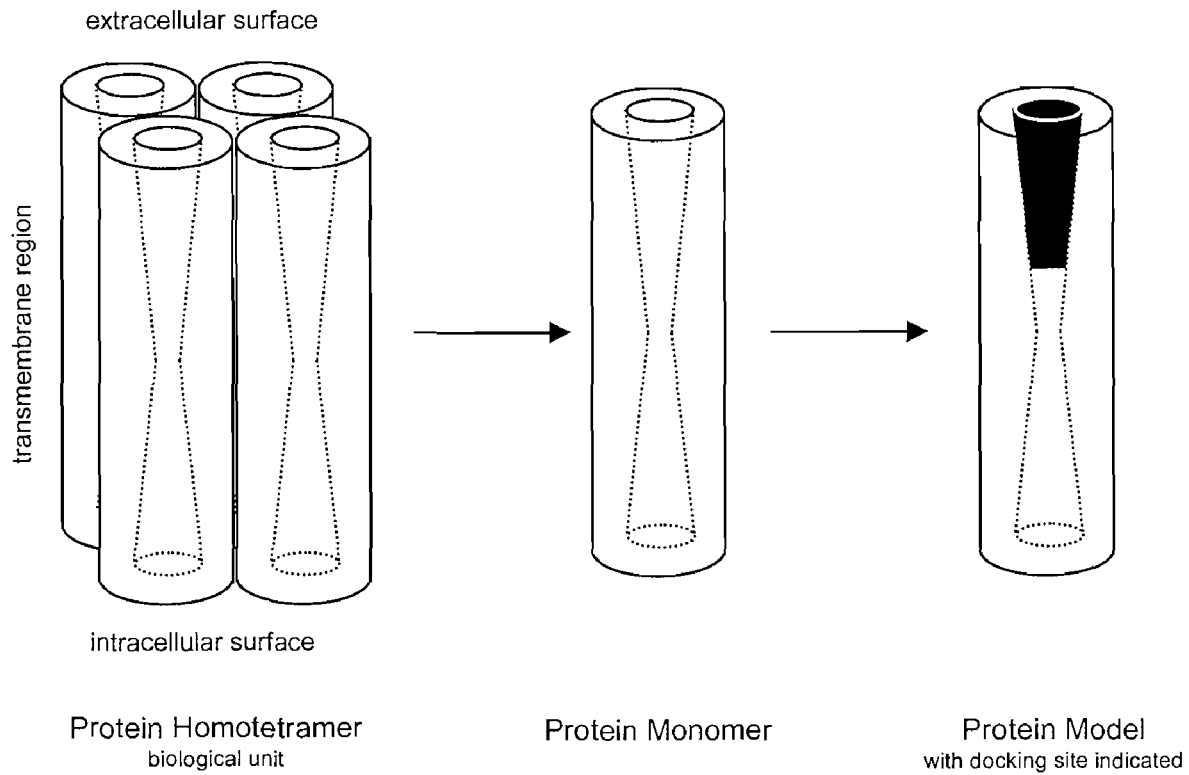
FIG. 13 represent schematic diagrams of AQP4 biological protein homotetramer structure and protein monomer model. The protein region used to define the docking site is indicated in black in the protein model diagram.

During the course of the invention described in this report, a model of the AQP4 protein monomer was built from a solid-state electron diffraction structure of the protein homotetramer (FIG. 13) (Hiroaki 2006). That AQP4 model was then used for in silico docking studies of various substrates into the mouth of the water channel. The protein residues relevant to the AQP4 binding were identified as being composed of residues Val-53, Thr-56, Trp-59, Asp-69, Phe-77, Gly-143, Gly-146, Val-147, Thr-148, Thr-149, His-151, His-201, Ile-205, Gly-209, Ala-210 and Arg-216. The docking energy and inhibitory percentage (% Inh) for a number of substrates was found to be correlated. Generally, compounds with weak or no inhibitory activity were found to have poorly stabilized docking energies, while those with strong inhibitory activities were found to have highly stabilized docking energies.

Figure 14:
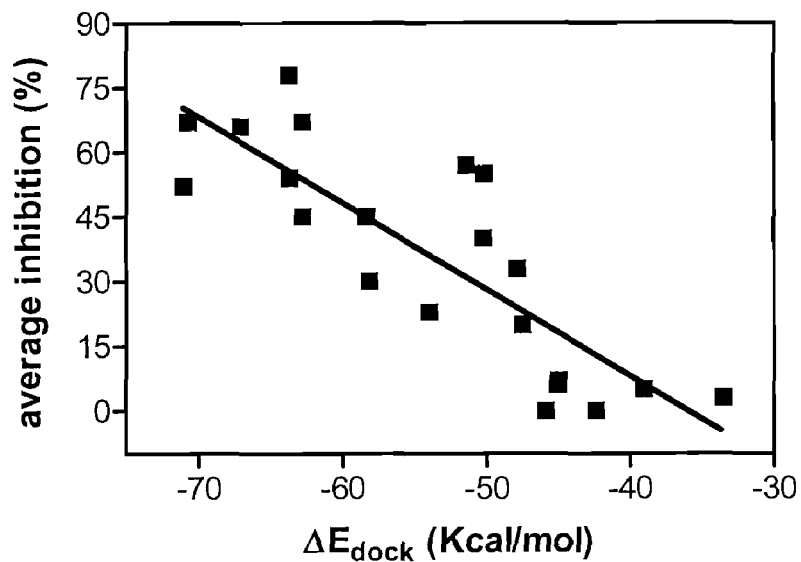
FIG. 14 is a graph showing correlation of docking energy of selected ligands to the extracellular mouth of the AQP4 protein monomer water channel, in Kcal/mol, and the percent inhibition of ligands ligands at 20 µM in an in vitro functional assay. Solid points represent the correlation of docking energy and percent inhibition of AQP4 mediated water transport by a specific ligand at 20 µM, solid line represents the linear least squares fit of the data. m=−2.01, $r^2$=0.70.

During the course of the invention described in this application, the correlation between the in vitro AQP4 inhibition and virtual assay docking energy was quantified. Plotting the in vitro AQP4 inhibition at 20 µM of the various chemical agents studied against their respective docking energy into the binding site defined for the protein monomer, as described above, gave a distribution of points that could be fit by a linear least-squares analysis (FIG. 14). The goodness of fit was quite high, $r^2$=0.70, which indicated that the docking energy obtained from the virtual docking simulation would be predictive of the ability of a given chemical agent's ability to reduce AQP4 mediated water transport.

The invention described herein can in part be described as pertaining to the identification of chemical agents that are able to inhibit the transport of water through AQP4. The identification of individual AQP4 inhibitors from the group of organic molecules described herein can be achieved by the comparison of AQP4 function both in the presence and absence of the chemical agent. Such a functional assay will, at a minimum, be described as being the analysis of a chemical compound using a biological substrate, such as a Xenopus oocyte or mammalian cell line that has been prepared such that it selectively expresses the AQP4 protein, or alternatively that natively expresses the AQP4 protein. The assay will be constructed, wherein an osmolar gradient will be created across the membrane of the biological substrate by varying the osmolarity of the external medium in contact with it, such that there will be a significant difference in the intra- and extracellular osmolarity. AQP4 inhibitor molecules can be identified as those with whom contact leads to a smaller changes in the oocyte or cellular volume relative to that observed in the absence of the chemical agent. Within the context of this invention, compatible biological substrates may be described as, but are not limited to Xenopus laevis oocytes, or alternatively CHO, COS, CACO, HEK or astrocyte cell lines, or the membranes or other derivatives thereof. Cells can be from human or other mammalian species in origin and may be further described as being immortal, transiently transfected or transformed as might be appropriate. Expression of AQP4 may be natural or alternatively may result from the introduction of an appropriate cRNA, cDNA, plasmid or other system that encodes for AQP4 expression, collectively referred to as an expression system. Such an expression system may be introduced by injection, viral transfer or another method as might be appropriate for the specific substrate. Changes in the osmolarity of the contacting medium can be affected by dilution, addition, flow-gradient, translocation of the substrate or another method, and can be done manually or through automation. Volumetric changes in the biological substrate can be monitored visually, by visible or fluorescent light spectroscopy, calorimetrically, potentiometrically, or by another means. Assay data can be evaluated manually, automatically or using some other method. Assay samples can be run individually, pooled in a combinatorial fashion or assayed in parallel with other individual samples. Experiments, can be conducted using 48, 96 or 384 well plates, either with round or flat bottoms. Alternatively, cells can be attached to either a microplate, as above, or another surface for which the contacting medium can be changed. Other formats are also possible depending on the specific type of biological substrate chosen for the assay. Preference is given for the use of a human isoform of AQP4; however, the uses of that protein derived from non-human species as described above is also possible as would be understood by an individual of normal skill in the artf.

The invention described herein can in part be described as pertaining to the identification of chemical agents that are able to inhibit the transport of water through AQP4. The identification of individual AQP4 inhibitors can be achieved by identifying their ability to bind to the protein in vitro. The AQP4 binding of a chemical agent can be revealed by measuring the displacement from the protein of a known AQP4 ligand, such as those described herein, which has been chemically modified such as to contain a fluorescent, photo-luminescent or radioactive group. Alternatively, AQP4 binding by a chemical agent can be revealed by measuring the retention of a radio-labeled homologue of those chemical agents described herein by a living cell, cell membrane or cell membrane fraction that contains AQP4, relative to one that is absent or significantly diminished in AQP4. Examples of the types of binding assays that would constitute this invention include but not limited to: radio-ligand displacement assays, fluorescence polarization assays and FRET assays. The assays can be performed manually or using laboratory automation on individual samples, those pooled in a combinatorial fashion or assayed in parallel with other individual samples. Assays can be conducted in 48, 96, 384 or 1536 well plates, the exact nature of which will depend on the specific assay, substrate used and the desired compound throughput. The AQP4 protein expressed and used in these assays is preferred as the human M1 or M23 isoform, but may alternatively be from another mammalian species including, but not limited to mouse, rat or horse, and the constructs made thereof.

The invention described herein can in part be described as pertaining to the identification of chemical agents that are able to inhibit the transport of water through AQP4. Individual examples of chemical agents can be selected for testing in in vitro assays such as those described herein, as well as ex vivo and in vivo on the basis of three-dimensional (3D) computational methods by which the presumed fit of the chemical agent to AQP4 is evaluated as utilized in the realization of this invention. Such 3D computational methods are commonly referred to as virtual or in silico screening, or alternatively as a virtual docking or simply as a docking simulation. At its simplest, these methods employ a 3D protein structure of AQP4 that has been derived from a solid-state or solution protein structure, or can alternatively be constructed from a homology model based the 3D structure of a related protein isozyme. The AQP4 3D structure can be either a homotetramer, which may also be described as the biological unit, or a protein monomer. Favored in this invention is the use of a protein monomer. The AQP4 protein model is read by a computer software program that can correlate the protein's steric, stereoelectronic and various energy terms with that which describes a potential organic chemical agent. Such a software program can evaluate the steric, stereoelectronic, and electronic compatibility of various conformations and placements of the ligand within the protein. A comparison of the resultant docking energies or docking scores between known and potential AQP4 inhibitors can be used as a means to select individual examples from the classes of compounds described herein. The computational simulation software used for this analysis can utilize classical (empirical), semi-empirical or ab initio based algorithms to evaluate a ligand's binding energy or docking score. The compounds to be investigated as described herein can be selected in a variety of ways, which includes but is not limited to individually, at random or from a virtual library of chemical substances.

The invention described herein can in part be described as pertaining to the identification of chemical agents that are able to inhibit the transport of water through AQP4. Individual examples of compounds can be selected for testing in in vitro assays such as those described herein, as well as for ex vivo and in vivo studies on the basis of a two-dimensional (2D) or three-dimensional (3D) comparison with known AQP4 inhibitory molecules, such as those described herein, using computational methods. At its simplest, these 2D or 3D comparative methods involve the computational determination of the chemicophysical properties of known AQP4 modulating compounds, correlation of those chemicophysical properties with observed in vitro or in vivo experimental results, and the subsequent identification of new compounds that share those important properties. The chemicophysical properties, sometimes referred to as descriptors, can include but are not limited to molecular weight, polarizable surface area, cLogP, dipole moment, molecular charge and total rotatable bonds. The active compounds used to correlate the important chemicophysical properties can be selected from known AQP4 modulator compounds, and in part be composed from the members of the class of compounds described herein. The compounds to be investigated can be selected in a variety of ways, which includes but is not limited to individually, at random or from a virtual library of chemical substances.

The invention described herein can in part be described as pertaining to the identification of chemical agents that are able to inhibit the transport of water through AQP4, and their uses as pharmacological agents for the treatment of human disease. These chemical agents described herein and preferred by this invention can be synthesized by chemical or biological means, or a combination thereof. The chemical synthesis of such agents can typically be achieved by a sequence of standard methods as would be understood by a practitioner of normal skill in the art. Such chemical synthesis can be realized on a scale that might be described as being between milligram and multi-kilogram, and may utilize a combination of enabling technologies such as but not limited to solution-phase synthesis, solid-phase synthesis, robotic synthesis, automated synthesis, partial automated synthesis, microwave accelerated synthesis, peptide synthesis, parallel synthesis, combinatorial synthesis and single-compound synthesis. Chemical agents as provided for in the invention can also be synthesized using biological or biochemical means, which might include but are not limited to phage display, cellular expression, digestion, enzymatic transformation and metabolic transformation. Chemical agents as provided for in the invention can also be synthesized using a combination of chemical and biological strategies, which would typically involve but are not limited to a sequence of chemical steps where one or more step is completed using an isolated enzyme, including but not limited to lipase, reductase, phosphotase or hydrolase, or where an intermediate is transformed using a whole cell or organism, such as but not limited to using liver cell culture, bacteria or yeast. Individual chemical agents that posses a chiral or asymmetric center can be synthesized such that the final product is pure or highly enriched in the desired stereoisomer, synthesized such that the final product is racemic, whereby the racemic product can be used as obtained or further resolved to give predominately one stereoisomer.

The invention described herein can in part be described as pertaining to the identification of chemical agents that are able to inhibit the transport of water through AQP4, and their uses as pharmacological agents for the treatment of human disease. The chemical agents described herein and preferred by this invention may be described as being a selective inhibitor of AQP4, a non-selective inhibitor of AQP4 isozymes that include AQP4, or a non-selective inhibitor of generally unrelated biological targets that include AQP4, as might be appropriate for the specific disease being treated and means of introducing the AQP4 inhibitory pharmaceutical product. Such an AQP4 inhibitory molecule can be used individually as a pharmaceutical agent, sometimes referred to as a monotherapy. However, also consistent within this embodiment of the invention is the possibility that an AQP4 inhibitory drug might also be compounded with a complimentary drug that interacts with a separate target not directly related to AQP4, such as would be consistent with a polytherapy or drug cocktail strategy. The choice of compounding drug would be dependent on the specific disease being treated, but might include without being limited to γ-aminobutyric acid receptor subtype-A ($GABA_A$-R) function modulators, sodium channel modulators, glutamate channel modulators, serotonin receptor modulators and carbonic anhydrase inhibitors. Also provided for in this invention are individual chemical agents that are able to inhibit the function of AQP4 while also modulating the function of another biological target so as to improve the overall potency and therapeutic utility of the pharmacological agent, and may be described as being a dual-mode drug. Such a dual-mode drug can be identified such that the molecule in its entirety is able to exert its effect in a predictable manner on AQP4 plus one or more additional targets, or alternatively by combining or fusing two or more individually identified moieties, one that primarily inhibits AQP4 with others that are preferential towards an alternative target, so as to improve the overall potency and therapeutic utility of the final drug substance.

The invention described herein can in part be described as pertaining to the identification of chemical agents that are able to inhibit the transport of water through AQP4, and their uses as pharmacological agents for the treatment of human disease. The chemical agents described herein or mixtures thereof with other pharmaceutical agents may be compounded is such a manner that they take on a number of physical appearances, as would appropriate to the specifics of the treatment, delivery and setting for which it will be used. These physical appearances include solid, semi-solid, liquid or gasses, such that can be used in but not limited to tablets, powders, wafers, polymeric matrices, crystals, granules, ointments, gels, suppositories, injections, inhalants, aerosols, rinses, sublinguants, eye drops, ear drops and transdermal patches, and may be administered by oral, rectal, intranasal, intravenous, intramuscular, transdermal or intrabronchial routes. The active pharmaceutical agents, as described herein, can be compounded with a variety of materials, the exact combination of which will be dependent on the disease, treatment setting, drug form and delivery method used, which may include but are not limited to binders, emulsifying agents, stabilizers, dispersants, buffering agents, conditioners, wetting agents, polymeric delivery agents and diluents, or other excipients. Such auxiliary agents may include but are not limited to cellulose, starch, dextrose, maltose, water, saline, glycerol, stearate, mineral oil, gelatin, ethyl alcohol, polyethylene glycol, propylene glycol, tween, sodium carbonate, sodium acetate, calcium hydroxide, calcium oxide, cyclodextrin, tartaric acid, guar gum, chlorofluorocarbons and hydrofluoralkanes, and other substances as would commonly be known to practitioners skilled in the art. The exact frequency of administration of the pharmaceutical formulation will differ depending on the specifics of the treatment regime, administration route and dosage format, as such the dosage frequency might include but is not limited to on demand tablets, nasal or oral inhalers, QD tablets, BID tablets, TID tablets, drops or inhalers, or others as warranted by the specific circumstances. The specific dosages of AQP4 inhibitor needed for therapeutic value can not be described directly because it is highly dependent on the treatment regime, pharmaceutical formulation, administration route, frequency and type of therapy. The particular details involved in formulation, dosage, format, frequency will be well understood by practitioners of normal skill in the art.

The invention described herein can in part be described as pertaining to the identification of chemical agents that are able to inhibit the transport of water through AQP4 and their uses in the treatment of human diseases. Preferred within the context of this invention are the treatment of diseases where modulation of AQP4 mediated water transport shows an efficacious benefit. These disease pathologies can include those that are directly caused by AQP4 and the function thereof, including but not limited to its mis-regulation or other mutational alterations, but can also include those pathologies where AQP4 plays a more passive role and that is not directly related its mis-regulation or mutational alterations.

A further description of types of pathologies for which the chemical agents described herein and their derivatives can be used as medicants as are provided for in this invention includes the treatment, prevention and prophylaxis of cerebral edema and disease pathologies related thereto. The condition of cerebral edema, and the general concept of brain swelling, may be acute or chronic in nature. Such pathology may be caused by a variety of situations, which may include but are not limited to trauma, acute water toxicity, hyponatremia, hypothermia, hypoxia, HACE, HAPE or hormone imbalance. Alternatively such edema might arise as a secondary consequence of a separate disease pathology, such as meningitis, Creutzfeldt-Jakob disease, lupus cerebritis, eclampsia, Reye's syndrome, diabetes mellitus, diabetic ketoacidosis, bacterial meningitis, viral meningitis, viral encephalitis, bacterial meningitis or a protozoan infection. Alternatively such edema may arise from acute ischemia or another ischemic insult. Alternatively such edema may be a result of overexposure to chemointoxicants, such as dinitrophenol, triethyltin, hexachlorophene or isoniazid, or other chemical and biological toxins. AQP4 inhibitors as described herein may be used as individual pharmaceutical agents in the treatment or prophylaxis of morbidity due to cerebral edema. Such inhibitory agents may also be used as one part of a drug-cocktail or polytherapy, wherein the combined combination of pharmaceutical agents shows a higher therapeutic index than any lesser combination thereof, and may include but are not limited to corticosteroids, diuretics, barbiturates, lidocaine, propofol, glycerol, mannitol or thrometamine.

A further description of types of pathologies for which the chemical agents described herein and their derivatives can be used as medicants as are provided for in this invention includes the prevention and prophylaxis of ischemia and ischemic injury. Within the context of this invention, the AQP4 inhibitors described herein can be utilized in the treatment of acute ischemia or a sudden ischemic state, which can arise from a cerebrovascular accident such as stroke, cardiac arrest, venous thrombosis, arterial thrombosis, tachycardia, hypotension or alternatively another situation. Such a situation may give rise to an infarct, and may be further related subsequent physical or cognitive impairment. Also within the scope of this invention, AQP4 inhibitors described herein can be used in the prevention of ischemic injury, where there is an elevated risk of an ischemic event, such as prior to surgery. Within the context of an acute ischemic event, the AQP4 inhibitory compound can be administered as early as possible, particularly before and during the reprofusion step. While it may therapeutically useful to use AQP4 inhibitors alone as the sole active component for the treatment of ischemia, it is also allowed within the scope of this invention for the AQP4 inhibitor to be part of a drug cocktail or polytherapy with other anti-ischemic agents such as but not limited to inhibitors of Caspase-family apoptosis initiators, antagonists of P53, glutamate receptor antagonists, calcium channel blockers, selective radical scavengers, and others as would be understood by individuals of normal skill in the art.

A further description of types of pathologies for which the chemical agents described herein and their derivatives can be used as medicants as are provided for in this invention includes the prevention or reduction of cerebral injury due to encephalitis. Such encephalitis may be acute or chronic in nature, and may arise from viral infections, as can be typified by that due to herpes simplex viruses, arboviruses, and others, bacterial infections, as can be typified by those due to syphilis and others, protozoal infections, such as that due to toxoplasma, among other potential causes. The primary effect of administering AQP4 inhibitory agents is to reduce the effect of, and injury from cerebral edema related to these disorders. The AQP4 inhibitory molecule can be administered as the sole active component, or alternatively as part of a drug-cocktail or polytherapy that might include, but is not limited to other drug agents, such as antivirals or antibiotics, that are specific for the encephalitis cause, or alternatively along with other pharmaceutical agents, such as corticosteroids, diuretics, barbiturates, lidocaine, propofol, glycerol, mannitol or thrometamine that can be used to control the degree of cerebral swelling.

A further description of types of pathologies for which the chemical agents described herein and their derivatives can be used as medicants as are provided for in this invention includes the prevention and prophylaxis of epilepsy, seizure and other involuntary convulsive disorders. While the specific causes of epilepsy and other involuntary convulsive disorders are often impossible to diagnose, these pathological conditions are often described as being related to the rapid depolarization and hyper-excitability of neurons. In many cases, these diseases can be defined as recurring seizures or involuntary convulsions that are not caused by obvious pathologies such as tumors, fever, edema, acute or chronic poisoning, meningitis or encephalitis, and may be revealed by observation, electroencephalography or a combination of both. The AQP4 inhibitory molecules as described herein can be utilized in the treatment of epileptic disorders that include but are not limited to West syndrome, childhood absence epilepsy, benign childhood epilepsy, juvenile myoclonic epilepsy, temporal lobe epilepsy, frontal lobe epilepsy, Lennox-Gastaut syndrome or occipital lobe epilepsy. Within the scope of this invention, AQP4 inhibitors can be used therapeutically in these disorders as a single agent, as could be described as monotherapy, or part of a drug cocktail in combination with other anti-epileptic drugs, as could be described as adjunctive therapy. In the context of an adjunctive therapy strategy, the AQP4 inhibitor might be used in combination of one or more anticonvulsant drugs, which might include but is not limited to acetazolamide, phenytoin, carbamazepine, oxcarbazepine, gabapentin, lamotrigine, topiramate, zonisamide, sodium valproate, valproic acid, primidone, tiagabine, vigabatrin, colazepam, ethosuximide, felbamate, fosphenytoin, flurazepam, levetiracetam, mephenytoin, phenobarbital, diazepam, lorazepam, paraldehyde and pentobarbital. Also provided for in this invention is the use of an AQP4 inhibitor as described herein, which has been designed to simultaneously interact selectively with another protein or transporter, examples of those targets particularly enjoyed in this invention are but not limited to modulators of $GABA_A$-R, $N_{VIR}4.1$, AMPA-R, GluR-4, NMDA-R, GABA transporter and $Ca_v3.1$. Also within the scope of this invention is the therapeutic use of AQP4 inhibitors in combination with other non-pharmacological treatments, including but not limited to surgical procedures, including palliative or respective surgeries, ketogenic diet or electro-stimulation.

A further description of types of pathologies for which the chemical agents described herein and their derivatives can be used as medicants as are provided for in this invention includes the prevention and prophylaxis of migraine. As revealed in the invention, AQP4 inhibitors as described herein can be utilized in the treatment of migraine or severe headache disorders that may be described as but not limited to migraine with aura, migraine without aura, basilar type migraine, familial hemiplegic migraine and acephalgic migraine. As being consistent with this invention, AQP4 inhibitory compounds may be used as a medicant in the treatment of migraine family disorders as either a prophylactic or during the initial onset as a means of rescue from the acute migraine symptoms. As described, these AQP4 inhibitors can be utilized individually or as part of a drug cocktail that shows greater therapeutic value than any of the individual components, within this context the AQP4 inhibitor may be combined therapeutically with known medicants for migraine prophylaxis and might include but is not limited to ergot amine, ergot amine derivatives, caffeine, nicotine, nicotine derivatives, lutalbital, fioricet, acetaminophen, acetylsalicylic acid, ibuprofen, barbiturates, codeine, morphine, amidrine, sumatriptan, zolmitriptan, naratriptan, rizatriptan, eletriptan, frovatriptan, almotriptan, namenda, sansert, sodium valproate, valproic acid, topiramate, phenytoin, zonisamide, carbamazepine, oxcarbazepine, phenytoin, acetazolamide, gabapentin, propranolol, atenolol, fluoxetine and amitriptyline. Also provided for in this invention is the use of an AQP4 inhibitory compound as described herein that has been developed to simultaneously and selectively modulate other protein targets for the purpose of improving the therapeutic value of the drug, these biological targets might include but are not limited to antagonists of the serotin receptors $5HT_{1B}$ and $5HT_{1D}$ and inhibitors of carbonic anhydrase family enzymes. Chemical agents that can inhibit AQP4 can also be used therapeutically with non-pharmacological treatments for migraine prophylaxis such as but not limited to electro-stimulation, transcranial magnetic stimulation and botox injection.

A further description of types of pathologies for which the chemical agents described herein and their derivatives can be used as medicants as are provided for in this invention includes the prevention and prophylaxis of dementia. As described, specific AQP4 inhibitory compounds from the provided for herein may be used in the treatment of dementia which may be related in part to that caused by Alzheimer's disease, vascular dementia, dementia with Lewy bodies, frontotemporal lobar degenerations, Creutzfeldt-Jakob disease or HIV syndrome, as well as those relating to other causes. As described, these AQP4 inhibitors can be utilized individually or as part of a drug cocktail that shows greater therapeutic value than any of the individual components, within this context the AQP4 inhibitor may be combined therapeutically with known medicants developed to treat the underlying pathology, and may include but are not limited to clopidogrel, eptifibatide, dipyridamole, acenocoumarol, dicumarol, phenprocoumon, phenindione, warfarin, antithrombin III, heparin, acetylsalicylic acid, indobufen, argatroban, desirudin, hirudin, melagatran, ximelagatran, dabigatran, citrate, EDTA, oxalate, memantine, donepezil, galanamine, rivastigmine, extracts of Ginko Bilboa leaf, flowers, nuts and the isolates thereof, leuprolide, R-flurbiprofen, tramiprosat, HAART, ritonavir, lopinavir, saquinavir, atazanavir, and others as would be understood to a practitioner of normal skill in the art.

A further description of types of pathologies for which the chemical agents described herein and their derivatives can be used as medicants as are provided for in this invention includes the treatment of drug addition. Within the context of this invention, AQP4 inhibitors can be used as the only pharmacologically active component or in combination with other pharmacologically active substances in the treatment of addition, withdrawal, and continued recovery. Such AQP4 inhibitors as identified herein can be used in combination with but not limited to specific modulators of GABAergic response.

A further description of types of pathologies for which the chemical agents described herein and their derivatives can be used as medicants as are provided for in this invention includes the prevention and prophylaxis of retinal ischemia. Within the context of the invention retinal ischemia can be due in part to optical surgery, ophthalmic artery occlusion, thromboembolism or giant cell arteritis. Individual AQP4 inhibitory compounds can be used as part of a monotherapy, or combined with other pharmaceutical agents wherein the therapeutic benefit of the combination is higher than that of any of the individual components. As described, these AQP4 inhibitors can be utilized individually or as part of a drug cocktail that shows greater therapeutic value than any of the individual components, within this context the AQP4 inhibitor may be combined therapeutically with known medicants developed to treat the underlying ischemic cause, and may include but are not limited to acenocoumarol, dicumarol, phenprocoumon, phenindione, warfarin, antithrombin III, heparin, acetylsalicylic acid, indobufen, argatroban, desirudin, hirudin, melagatran, ximelagatran, dabigatran, citrate, EDTA, oxalate, and others as would be known to a person with normal skill in the art.

A further description of types of pathologies for which the chemical agents described herein and their derivatives can be used as medicants as are provided for in this invention includes the treatment and prophylaxis of glaucoma. Within the context of the invention, AQP4 inhibitory chemical agents can be utilized individually or as part of a drug cocktail in part to reduce the intraocular pressure and limit damage to Müller cells, retinal cells and optic nerve. Preferred by the invention is the use of AQP4 inhibitory agents in combination with pharmaceutical drugs including but not limited to latanoprost, bimatoprost, travaoprost, timolol, levobunolol, betaxolol, brimonidine, epinephrine, dipivefrin, pilocarpine, dorzolamide, brinzolamide, acetazolamide or dronabinol, whereby the overall therapeutic benefit of the drug combination is higher than that of the individual components. Also provided for in this invention is the use of an AQP4 inhibitory compound as described herein that has been developed to simultaneously and selectively modulate other protein targets for the purpose of improving the therapeutic value of the drug, these biological targets might include but are not limited to antagonists of carbonic anhydrase, as well as modulators of CA1 and CA2, FAAH, $a_2$, $beta_1$, AQP0, AQP1, AQP3 or AQP5. Inhibitors of AQP4, as described in the invention, may also be expected to show therapeutic benefit when used in combination with surgical treatments.

A further description of types of pathologies for which the chemical agents described herein and their derivatives can be used as medicants as are provided for in this invention includes the prevention and prophylaxis of ocular disease such as but not limited to retinopathy and keratopathy.

A further description of types of pathologies for which the chemical agents described herein and their derivatives can be used as medicants as are provided for in this invention includes the treatment of tumors and cancerous growths. Preferred by this aspect of the invention is the use of AQP4 inhibitory agents described herein as part of a treatment regimen for low grade astrocytomas, glioma, and adenocarcinomas, as well as other types of brain tumor. The administration of AQP4 inhibitory agents can primarily be part of a polytherapy, which includes but is not limited to radiation treatment, surgery or treatment when anti-cancer chemotherapeutic agents as the primary means of treatment. Such AQP4 inhibitory compounds can also be utilized in the treatment of cancers of the periphery wherein the cancer or tumor type is characterized by an expressional upregulation of AQP4. The individual AQP4 inhibitory compounds described herein can be used individually or as part of a polytherapy in combination with other pharmaceutical agents used to treat cancer and cancerous growths, which might include but are not limited to cisplatin, carboplatin, cyclophosphamide, paclitaxel, methotrexate, fludarabine, floxuridine, vincristine, irinotecan, amsacrine, and others that would be known to individuals of normal skill in the art. Also envisioned is the use of such AQP4 inhibitory agents with other non-pharmacological cancer treatment which might include but are not limited to radiation treatment or surgery, such as would be understood by an individual of normal skill in the art.

A further description of types of pathologies for which the chemical agents described herein and their derivatives can be used as medicants, as provided for in this invention, includes the prevention and prophylaxis of Meniere's disease. Within the context of the invention, AQP4 inhibitors identified herein could be utilized individually or as part of a drug cocktail or polytherapy in part to restore fluid balance to the inner ear. Within the context of a drug cocktail or poly-therapy, AQP4 inhibitors can be administered in combination with antihistamines, anticholinergics, steroids and diuretics, such that the therapeutic benefit of the combined pharmaceutical agents is greater than that of each individual component, and may include but is not limited to mepyramine, antazoline, diphenhydramine, carbinoxamine, doxylamine, clemastine, dimenhydrinate, pheniramine, chlorphenamine, dexchlorphenamine, bropheniramine, triprolidine, cyclizine, chlorcyclizine, hydroxyzine, meclizine, promethazine, alimemazine, cyproheptadine, azatadine, ketotifen, acrivastine, astemizole, cetirizine, loratadine, mizolastine, terfenadine, fexofenadine, azelastine, levocabastine, olopatadine, levocetirizine, desloratadine, fexofenadine, cromoglicate, nedocromil, cimetidine, ranitidine, famotidine, thioperamide, clobenpropit, impromidine, benztropine, scopolamine, atropine, dicyclomine, flavoxate, ipratropium, tropicamide, trimethaphan, atracurium, doxacurium, suxamethonium chloride, hydrocortisone, cortisone acetate, prednisone, prednisolone, methylprednisolone, dexamethasone, betametasone, fludrocortisone acetate, deoxycorticosterone acetate, aldosterone, mannitol, acetazolamide, dorzolamide, caffeine or theophylline. Also provided for in this invention is the use of an AQP4 inhibitory compound as described herein that has been developed to simultaneously and selectively modulate other protein targets for the purpose of improving the therapeutic value of the drug, these biological targets might include but are not limited to antagonists of $H_1$, $H_2$, $M_1$, $M_2$, $nAChR_x$, $CA_2$ and $CA_4$.

What is claimed is:

1. An inhibitory modulator of AQP4 protein, wherein the modulator binds to the AQP4 protein, and inhibits AQP4 mediated water transport, and wherein said modulator is represented by the following formula:

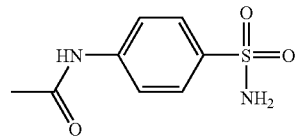

or a pharmaceutically acceptable salt thereof.

2. A method for inhibiting AQP4 mediated water transport, comprising dosing the inhibitory modulator of AQP4 according to claim 1, and binding the modulator to the AQP4 protein.

* * * * *